United States Patent [19]
Graham et al.

[11] Patent Number: 5,760,045
[45] Date of Patent: Jun. 2, 1998

[54] DELTA-17 AND DELTA-20 OLEFINIC AND SATURATED 17β-SUBSTITUTED-4-AZA-5α-ANDROSTAN-3-ONES AS 5α-REDUCTASE INHIBITORS USEFUL IN THE PREVENTION AND TREATMENT OF HYPERANDROGENIC DISORDERS

[75] Inventors: Donald W. Graham, Mountainside; Susan D. Aster, Teaneck; Richard L. Tolman, Warren, all of N.J.

[73] Assignee: Merck & Co., Inc., Rahway, N.J.

[21] Appl. No.: 595,946

[22] Filed: Feb. 6, 1996

Related U.S. Application Data

[60] Division of Ser. No. 338,490, Nov. 14, 1994, Pat. No. 5,510,351, which is a continuation-in-part of Ser. No. 886,050, May 20, 1992, abandoned.

[51] Int. Cl.$^6$ .................... C07D 241/12; A61K 31/495
[52] U.S. Cl. ................................ 514/284; 546/77
[58] Field of Search .................. 546/77; 514/284

[56] References Cited

U.S. PATENT DOCUMENTS

| | | | |
|---|---|---|---|
| 4,220,775 | 9/1980 | Rasmusson et al. | 546/77 |
| 4,377,584 | 3/1983 | Rasmusson et al. | 546/77 |
| 4,596,812 | 6/1986 | Chidsey, III et al. | |
| 4,732,897 | 3/1988 | Cainelli | 546/77 |
| 4,760,071 | 7/1988 | Rasmusson et al. | 546/77 |
| 4,859,681 | 8/1989 | Rasmusson et al. | 546/77 |
| 4,882,319 | 11/1989 | Holt et al. | 514/71 |
| 4,888,336 | 12/1989 | Holt et al. | 546/77 |
| 4,910,226 | 3/1990 | Holt et al. | 514/319 |
| 5,049,562 | 9/1991 | Rasmusson et al. | 546/77 |
| 5,084,574 | 1/1992 | Bhattachayra et al. | |
| 5,110,939 | 5/1992 | Holt | |
| 5,116,983 | 5/1992 | Bhattacharya et al. | |
| 5,120,742 | 6/1992 | Rasmusson et al. | 546/77 |
| 5,175,155 | 12/1992 | Juniewicz et al. | 514/284 |
| 5,510,351 | 4/1996 | Graham et al. | 514/284 |
| 5,510,485 | 4/1996 | Graham et al. | 546/77 |
| 5,595,996 | 1/1997 | Graham et al. | 546/77 |

FOREIGN PATENT DOCUMENTS

| | | |
|---|---|---|
| 0 004 949 | 10/1979 | European Pat. Off. |
| 0 200 859 | 11/1986 | European Pat. Off. |
| 0 277 002 | 6/1988 | European Pat. Off. |
| 0 298 652 | 1/1989 | European Pat. Off. |
| 0 572 166 | 12/1993 | European Pat. Off. |
| 1465544 | 11/1965 | France |
| WO 93/23039 | 11/1993 | WIPO |
| WO 94/00125 | 1/1994 | WIPO |

OTHER PUBLICATIONS

The Daily (Tuesday, May 7, 1996), "New Data on Proscar, Abbott's Hytrin Show Conflicting Results".

Wall Street Journal (Tuesday, May 7, 1996), "Study Finds Abbott's Prostate Drug is Much More Effective than Merck's", p. B4.

US News & World Report, May 20, 1996, "Zapping a problem prostate".

Rasmusson et al., J. Med. Chem., 29(11), (1986), pp. 2298–2315, "Aza steroids: structure–activity relationships . . . ".

Brooks et al. Prostate (1986), 9(1), pp. 65–75, "Prostatic effects induced in dogs by . . . 5 alpha–reductase inhibitors".

Brooks et al., Steroids (1986), 47(1), pp. 1–19, "5 alpha–reductase inhibitory . . . activities of some 4–aza–steroids in the rat".

Liang et al., Endo. (1985) 117(2), pp. 571–579, "Species differences in prostatic steroidal 5 alpha–reductases of rat, dog, and human".

Rasmusson et al., J. Med. Chem. (1984) 27(12), pp. 1690–1701, "Azasteroids as inhibitors of rat prostatic 5 alpha–reductase".

Kadohama et al., JNCL, vol. 74, No. 2, pp. 475–481, "Retardation of prostate tumor progression in the noble rat by 4–methyl–4–aza–steroidal inhibitors of 5 alpha–reductas".

Brooks et al., Steroids, vol. 18 (1991), pp. 215–227, "Effect of castration, DES, flutamide, and MK–906 on growth of the dunning rat prostatic carcinoma . . . ".

Labrie et al., Lancet, (1986), No. 8515, pp. 1095–1096, "Combination therapy in prostate cancer".

Stinson, Chem & Eng News (Jun. 29, 1992), pp. 7–8, "Prostate drug Proscar cleared for marketing".

Helliker, Wall Street Journal (Jun. 7, 1991), pp. A1 and A7, "Alopecia sufferers seek to suffer less and not in silence"

Burger, Medicinal Chemistry 2nd ed., Interscience , New York (1960), p. 42.

Burger, "Medicinal Chemistry 2nd ed.", Interscience, New York (1960), p. 42.

Back et al., J. Organic Chem., vol 54 (1989), pp. 1904–1910 "N–chloroazasteroids: a novel class of reactive steroid analogues . . . ".

Diani et al., J. Clin. Endoc. and Metab., vol. 74, No. 2, pp. 345–350 (1990), "Hair growth effects of oral administration of finasteride".

Geldof et al., J. Cancer Res. Clin. Oncol., vol. 118 (1992), pp. 50–55, "Consideration of the use of . . . 4MA . . . in prostate cancer therapy".

*Primary Examiner*—Donald G. Daus
*Attorney, Agent, or Firm*—Catherine D. Fitch; Melvin Winokur

[57] ABSTRACT

Described are new delta-17 and delta-20 olefic and saturated 17β-substituted 4-aza-5α-androstan-3-ones and related compounds and the use of such compounds as 5α-reductase inhibitors for treatment of benign prostatic hyperplasia and other hyperandrogenic related disorders.

9 Claims, No Drawings

DELTA-17 AND DELTA-20 OLEFINIC AND SATURATED 17β-SUBSTITUTED-4-AZA-5α-ANDROSTAN-3-ONES AS 5α-REDUCTASE INHIBITORS USEFUL IN THE PREVENTION AND TREATMENT OF HYPERANDROGENIC DISORDERS

CROSS REFERENCE TO RELATED APPLICATIONS

This application is a divisional of application Ser. No. 08/338,490, filed Nov. 14, 1994, U.S. Pat. No. 5,510,351 which in turn is a national phase application under 35 U.S.C. §371 of PCT/US93/04630, filed May 17, 1993, which in turn is a continuation-in-part of application Ser. No. 886,050, filed May 20, 1992, now abandoned.

BACKGROUND OF THE INVENTION

The present invention is directed to new delta-17 and delta-20 olefinic and saturated 17β-substituted 4-aza-5α-androstan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hyperplasia, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs, e.g. the prostate, is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation. For example, a number of 4-aza steroid compounds are known which are 5α-reductase inhibitors.

See the following Merck & Co., Inc. patents, U.S. Pat. Nos. 4,377,584, 4,220,775, 4,859,681, 4,760,071 and the articles J. Med. Chem. 27, p. 1690–1701 (1984) and J. Med. Chem. 22, 2998–2315 (1986) of Rasmusson, et al., and U.S. Pat. No. 4,845,104 to Carlin, et al., and U.S. Pat. No. 4,732,897 to Cainelli, et al. which describe 4-aza-17β-substituted-5α-androstan-3-ones said to be useful in the treatment of DHT-related hyperandrogenic conditions.

Further there is the suggestion in the early prior art that hyperandrogenic diseases are the result of a single 5α-reductase. However, there are later reports regarding the presence of other 5α-reductase iszymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases in rats. This rat gene was later used to identify a human prostatic cDNA encoding a 5a-reductase termed "5α-reductase 1". (See Proc. Nat'l. Acad. Sci. 87, p. 3640–3644, 1990.)

More recently, a second, human prostatic reductase (5α-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson suggests that the 5α-reductase 1 enzyme is associated with hair follicles.

Thus, the art supports the existence of at least two genes for 5α-reductase and two distinct isozymes of 5α-reductase in humans. Both isozymes are believed to be present in prostatic tissue in which, 5α-reductase 2, is the more abundant, while the other isozyme, 5α-reductase 1, is believed to be more abundant in scalp tissue.

In the treatment of hyperandrogenic disease conditions, e.g. benign prostatic hyperplasia (BPH) it would be desirable to have one drug entity which is dually active against both enzymes 1 and 2 in the prostate to substantially inhibit dihydrotesterone (DHT) production. Alternatively, it would be desirable to have a drug entity which is highly selective for inhibiting the scalp-associated enzyme 5α-reductase 2. The drug could also be used in combination with PROSCAR® (finasteride) which is highly selective for the prostatic enzyme 5α-reductase 2 for combination therapy in the treatment of BPH.

SUMMARY OF THE INVENTION

The present invention discloses novel delta-17 and delta-20 olefinic-and saturated 17β-substituted-4-aza-5α-androstan-3-one compounds which are useful for inhibiting the 5α-reductase enzyme and isozymes thereof in prostatic tissue. They are also particularly effective in selectively inhibiting the 5α-reductase 1 associated with the scalp and/or dually inhibiting both isozymes 1 and 2 in the oral, parenteral or topical treatment of benign prostatic hyperplasia, acne, female hirsutism, androgenic alopecia, i.e., male pattern baldness, prostatitis, and the treatment of prostatic carcinoma.

In accordance with the present invention there is provided novel 17β-substituted olefinic and saturated 4-aza-5α-androstan-3-one and related compounds of the formula:

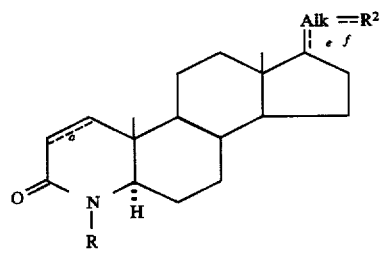

wherein:

Alk is $C_1$–$C_4$ straight or branched chain alkyl or alkenyl;
dashed lines a, e and f each can independently represent a double bond when present, with the proviso that double bonds formed by e and f are not both present concurrently;

R is selected from hydrogen, methyl or ethyl;

$R^2$ is (a) $C_6-C_{10}$ aryl, cyano, a 5–6 membered heteroaryl radical, which can contain 1–4 nitrogen atom, one oxygen or sulfur atoms or combinations thereof with 1–2 nitrogen atoms, providing that where $R^2$ is cyano, double bonds e and f are not present;

(b) $COR_1$, where $R_1$ is $C_6-C_{10}$ aryl, substituted $C_6-C_{10}$ aryl, and heteroaryl;

(c) $CONHR_2$, where $R_2$ is substituted phenyl, heteroaryl, substituted heteroaryl, or $C_7$ to $C_{12}$ cycloalkyl;

(d) $CO_2R_3$, where $R_3$ is $C_1-C_{18}$ linear or branched alkyl, $C_6-C_{10}$ aryl, substituted $C_6-C_{10}$ aryl, or $C_7-C_{12}$ cycloalkyl; providing that in (b), (c) and (d), Alk can only be alkenyl;

wherein the above aryl or heteroaryl radicals can also be fused with a benzo or another heteroraryl ring and can further be substituted with one or more substitutents; and pharmaceutically acceptable salts and esters thereof.

Further provided is a compound of the formula:

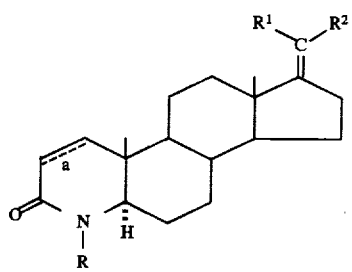

wherein the dashed line a represents a double bond when present;

R and $R^1$ are selected from hydrogen, methyl and ethyl; and $R^2$ is as defined above, including both (E) and (Z) forms, and mixtures thereof.

Also provided is a compound of claim 1 of the formula:

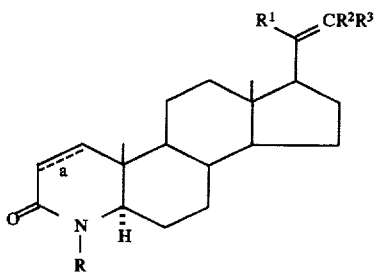

wherein the dashed line a can represent a double bond when present,

R, $R^1$ and $R^3$ are independently selected from hydrogen, methyl and ethyl, with the proviso that at least one of $R^1$ and $R^3$ is hydrogen, $R^2$ is (a) $C_6-C_{10}$ aryl or heteroaryl as defined above, and $R^2$ and $R^3$ can be in a E or Z bond configuration;

(b) $COR_1$, where $R_1$ is $C_6-C_{10}$ aryl, substituted $C_6-C_{10}$ aryl, and heteroaryl;

(c) $CONHR_2$, where $R_2$ is substituted-phenyl, heteroaryl, substituted heteroaryl, or $C_7$ to $C_{12}$ cycloalkyl;

(d) $CO_2R_3$, where $R_3$ is $C_1-C_{18}$ linear or branched alkyl, $C_6-C_{10}$ aryl, substituted $C_6-C_{10}$ aryl, or $C_7-C_{12}$ cycloalkyl; providing that in (b), (c) and (d), Alk can only be alkenyl; and mixed thereof.

Additionally, there is provided a compound of the formula:

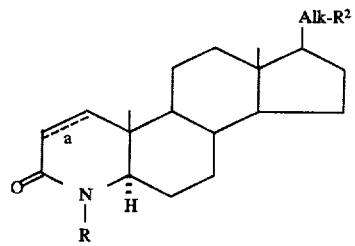

wherein:

Alk is $C_1-C_4$ straight or branched chain alkyl; dashed line a can represent a double bond when present;

R is selected from hydrogen, methyl or ethyl; and $R^2$ is as defined above.

Also specifically provided is a compound of structure IVA of the formula:

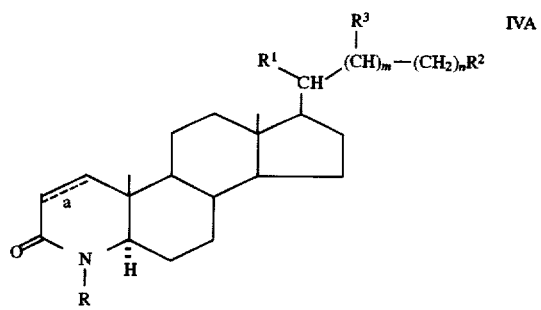

wherein the dashed line a can represent a double bond when present, and m is 0–1, n is 0–3;and R, $R^1$ and $R^3$ are independently selected from hydrogen, methyl and ethyl, with the proviso that at least one of $R^1$ and $R^3$ is hydrogen, $R^2$ is $C_6-C_{10}$ aryl, cyano, or heteroaryl as defined above.

Also disclosed are processes for their preparation, pharmaceutical formulations comprising the novel compounds as active ingredients and methods of inhibiting 5α-reductases 1 and/or 2 in diseases which occur under hyperandrogenic conditions, e.g., benign prostatic hyperplasia.

DETAILED DESCRIPTION OF THE INVENTION AND PREFERRED EMBODIMENTS

The structures I–IV above encompass all the 5α-reductase inhibitor compounds of this invention.

By the term "Alk" is meant $C_1-C_4$ or branched alkyl or alkenyl; e.g. methyl, ethyl, isopropyl, propyl, n-butyl, isobutyl, sec-butyl, ethenyl, propenyl, isopropenyl, 1- and 2-butenyl and the like.

Where the double bond "e" is present, the compounds are delta-17 olefins and where the double bond "f" is present, the compounds are delta-20 olefins. Note that dashed lines "e" and "f" both cannot be double bonds concurrently.

Dashed line "a" can independently be a double bond and when present, the compound is a 1-ene.

$R^2$ is a $C_6-C_{10}$ aryl including phenyl, benzyl, 1- and 2-phenethyl and naphthyl, and also cyano.

Preferred is where $R^2$ aryl is phenyl or cyano.

$R^2$ can also be 5–6 membered heteroaryl radical being fully unsaturated containing 1–4 nitrogen atoms, e.g. pyridyl, pyrryl, imidazolyl, tetrazolyl, pyrazinyl, pyrimidinyl, pyrazolyl, or triazolyl; containing 1–2 oxygen or sulfur atoms, e.g. thienyl, furanyl; or in combination with 1–2 nitrogen atoms, e.g. isothiazolyl, thiazolyl, isoxazolyl, oxazolyl or thiadiazolyl; or fused with a benzo ring, e.g. quinolyl, isoquinolyl, benzothienyl, isobenzofuryl, indolyl, carbazolyl; or fused with another heteroaryl ring, e.g. purinyl, and the like.

Preferred examples are 2-, 3-, and 4-pyridyl, 2-thienyl; 2-pyrazinyl, 2-, 4-, and 5-thiazolyl.

The $R^2$ aryl or heteroaryl ring can be unsubstituted or substituted with one or more of the following substituents providing the substitution leads to a chemically inert, but biologically active $5\alpha$ reductase inhibitor.

The $R^2$ ring substituents include:

$C_1$–$C_{18}$ straight or branched alkyl; e.g. methyl, ethyl, propyl, isopropyl, n-butyl, sec-butyl, isobutyl, t-butyl, n-pentyl, n-hexyl, iso-hexyl, n-butyl, n-octyl, iso-octyl, t-octyl, n-decyl, n-dodecyl, isooctodecyl, and the like;

$C_2$–$C_8$ straight or branched alkenyl, e.g. ethenyl, 1-propenyl, 2-propenyl, 1-butenyl, 2-butenyl, 3-butenyl, 1-pentenyl, 1-hexenyl, 1-heptenyl, 1-octenyl, 2-octenyl, and the like;

$C_3$–$C_8$ cycloalkyl e.g., cyclopropyl, cyclobutyl, cyclopentyl, cyclohexyl, 1-methylcyclobutyl, cyclopentyl, cyclohexyl, 1-methylcyclohexyl, 2-methylcyclohexyl, 2-ethylcyclohexyl, and the like;

$C_2$–$C_8$ alkynyl e.g., 1-ethynyl; 1-propynyl, 2-propynyl, 2-butynyl, 2-pentynyl, 1-hexynyl, 1-heptynyl, 1-octynyl;

$CONR^4R^5$ where $R^4$ and $R^5$ independently are H, $C_1$–$C_8$ alkyl, as defined above, $C_3$–$C_8$ cycloalkyl as defined above, $C_1$–$C_4$ perhaloalkyl e.g., trifluoromethyl, perfluoromethyl, trichloromethyl, preferably perfluoroalkyl; phenyl, or substituted phenyl, as described below;

$COR^4$, where $R^4$ is defined above, including acetyl, isobutylcarbonyl, benzoyl and the like;

$S(O)_nR^4$, where n is 0–2 and $R^4$ is defined above, including methylsulfinyl, methylsulfonyl, phenylsulfonyl, 4-chlorophenylsulfinyl and the like;

$OCOR^4$, where $R^4$ is defined above, including acetoxy, propionyloxy, benzoyloxy, 4-chlorobenzoyloxy and the like.

$SO_2NR^4R^5$ where $R^4$ and $R^5$ are described above, including sulfonamido, N-methylsulfonamido, N-phenylsulfonamido, N,N-dimethylsulfonamido and the like;

$NR^4(CO)R^5$, wherein $R^4$ and $R^5$ are defined above, including; acetylamino, benzoylamino, N-methylbenzoylamino and the like;

$NR^4(CO)NHR^5$, wherein $R^4$ and $R^5$ are described above, including; ureido, N-methylureido, N-methyl-$N^1$-phenylureido and the like;

$NHSO_2R^4$, $R^4$ being defined above, including methylsulfonylamino, phenylsulfonylamino and the like;

$OR^4$, where $R^4$ is defined above, including methoxy, phenoxy, 4-chlorophenoxy and the like.

$NR^4R^5$, wherein $R^4$ and $R^5$ are described above, including amino, methylamino, dimethylamino, anilino and the like;

Cyano, nitro, halo, including: fluoro, chloro, bromo and iodo;

Perhalo $C_1$–$C_4$ alkyl, including: trifluoromethyl, perfluoroethyl, trichloromethyl and the like.

$CO_2R^4$, wherein $R^4$ is defined above, including $CO_2CH_3$, $CO_2Ph$, $CO_2$-(1-adamantyl) and the like; phenyl and substituted phenyl of the formula:

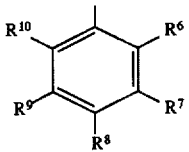

wherein the radicals $R^6$–$R^{10}$ each can represent one or more of the substituents defined above, including; hydrogen, 4-chlorophenyl, 4-fluorophenyl, 4-methoxyphenyl, 4-phenoxy and the like.

Unless otherwise indicated, the 17-position substituent is in the beta configuration.

Representative compounds of the present invention include the following:

(17E)-17-[phenyl)methylene]-4-methyl-4-aza-5α-androstan-3-one, ((17E)-17-[(4-chlorophenyl)methylene]-4-methyl-4-aza-5α-androstan-3-one, (17E)-17-[(3-chlorophenyl)methylene]-4-methyl-4-aza-5α-androstan-3-one, (17E)-17-[(2-chlorophenyl)methylene]-4-methyl-4-aza-5α-androstan-3-one, (17E)-17-[(4-ethoxycarbonylphenyl)methyl-ene]-4-methyl-4-aza-5α-androstan-one, (17E)-17-[(4-carboxyphenyl)methylene]-4-methyl-4-aza-5α-androstan-3-one, (17E)-17-[4-[[(1,1-dimethylethyl)amino)carbonyl]phenyl]-methylene]-4-methyl-4-aza-5α-androstan-3-one, (17E)-17-[(3,4,5-trimethoxyphenyl)methyl-ene]-4-aza-5α-androstan-3-one, (17E)-17-[(2-methoxyphenyl)methylene]-4-methyl-4-aza-5α-androstan-3-one, (17E)-17-[(4-methylsulfonylphenyl)methyl-ene]4-methyl-4-aza-5α-androstan-3-one, (17E)-17-[(4-biphenyl)methylene]-4-aza-5α-androstan-3-one, (17E)-17-[(4-nitrophenyl)methylene]-4-methyl-4-aza-5α-androstan-3-one, (17E)-17-[(4-aminophenyl)methylene]-4-aza-5α-androstan-3-one, (17E)-17-[(4-acetylaminophenyl)methylene]-4-methyl-4-aza-5α-androstan-3 -one, (17E)-17-(4-pivaloylaminophenyl)methylene)-4-methyl-4-aza-5α-androstan-3-one, (17E)-17-[(4-phenoxyphenyl)methylene]4-aza-5α-androstan-3-one, (17E)-17-[(2-imidazolyl)methylene]-4-methyl-4-aza-5α-androst-1-en-3-one, (17E)-17-[(2-thiazolyl)methylene]-4-aza-5α-androst-1-en-3-one, (17E)-17-[(2-pyrazinyl)methylene]-4-methyl-4-aza-5α-androstan-3-one, (17E)-20-phenyl-4-methyl-4-aza-5α-pregn-17-en-3-one, (17E)-20-[(4-chloro)phenyl]-4-aza-5α-pregn-17-en-3-one, (20E)4-methyl-21-[(4-methoxy)phenyl]-4-aza-5α-pregn-20-en-3-one, (20E)-4-methyl-21-phenyl-4-aza-5α-pregn-20-en-3-one, (20E)-4-methyl-21-[(4-methyl)phenyl]-4-aza-5α-pregn-20-en-3-one, (20E)-4-methyl-21-[(4-chloro)phenyl]-4-aza-5α-pregn-20-en-3-one, (20E)-4-methyl-21-(4-pyridyl)-4-aza-5α-pregn-20-en-3-one, (20E)-4-methyl-21-[(3-chloro)phenyl]-4-aza-5α-pregn-20-en-3-one,
(20E)-4-methyl-21-[(2-chloro)phenyl]-4-aza-5α-pregn-20-en-3-one,
(20E)-4-methyl-21-(2-pyridyl)-4-aza-5α-pregn-20-en-3-one,
(20E)-4-methyl-21-(2-thienyl)-4-aza-5α-pregn-20-en-3-one,
(20E)-21-[(4-methoxy)phenyl]-4-aza-5α-pregn-20-en-3-one,
(20E)-4-methyl-21-(3-thienyl)-4-aza-5α-pregn-20-en-3-one,
(20E)-4-methyl-21-(2-furanyl)-4-aza-5α-pregn-20-en-3-one,
(20E)-4-methyl-21-[(2-fluoro)phenyl]-4-aza-5α-pregn-20-en-3-one,
(20E)-21-(4-pyridyl)-4-aza-5α-pregn-1,20-dien-3-one,
(20E)-21-(4-pyridyl)4-aza-5α-pregn-20-en-3-one,
(20E)-21-[(4-methoxy)phenyl]-4-aza-5α-pregn-1,20-dien-3-one,
(20E)-21-(2-furanyl)-4-aza-5α-pregn-1,20-dien-3-one,
(20E)-21-(2-pyridyl)-4-aza-5α-pregn-1,20-dien-3-one,
(20E)-21-(3-pyridyl)-4-aza-5α-pregn-1,20-dien-3-one
(20E)-21-[(4-ethoxycarbonyl)phenyl]-4-aza-5α-pregn-1,20-dien-3-one,
(20E)-21-4-[N-phenyl]benzamido-4-aza-5α-pregn-1,20-dien-3-one,
(20E)-21-(2-pyridyl)-4-aza-5α-pregn-20-en-3-one,
(20E)-21-(3-pyridyl)-4-aza-5α-pregn-20-en-3-one,
(20E)-21-(2-thienyl)-4-aza-5α-pregn-20-en-3-one,
(20E)-4,20-dimethyl-21-phenyl-4-aza-5α-pregn-20-en-3-one,
(20E)-4,20-dimethyl-21-(4-chlorophenyl)-4-aza-5α-pregn-20-en-3-one,
(20E)-4,20-dimethyl-21-(2-thienyl)-4-aza-5α-pregn-20-en-3-one,
(20E)-4,20-dimethyl-21-(2-pyridyl)-4-aza-5α-pregn-20-en-3-one,
(20E)-20-methyl-21-(4-pyridyl)-4-aza-5α-pregna-1,20-dien-3-one,
(20E)-4,20-dimethyl-21-(4-pyridyl)-4-aza-5α-pregn-20-en-3-one,
(20E)-20-methyl-21-(2-furyl)-4-aza-5α-pregna-1,20-dien-3-one,
(20E)-20-methyl-21-(2-pyridyl)-4-aza-5α-pregna-1,20-dien-3-one,
(20E)-20-ethyl-21-phenyl-4-aza-5α-pregna-1,20-dien-3-one,
(20E)-20-ethyl-21-(2-pyridyl)-4-aza-5α-pregna-1,20-dien-3-one,
20(E,Z)-4,21-dimethyl-21-phenyl-4-aza-5α-pregn-20-en-3-one,
20(E,Z)-21-methyl-21-(4-chlorophenyl)-4-aza-5α-pregn-20-en-3-one,
20(E,Z)-4,21-dimethyl-21-(2-pyridyl)-4-aza-5α-pregn-1,20-dien-3-one,
17β-[(4-chlorophenyl)methyl]-4-methyl-4-aza-5α-androstan-3-one,
17β-[(phenyl)methyl]-4-aza-5α-androstan-3-one,
17β-[(2-pyridyl)methyl]-4-methyl-4-aza-5α-androst-1-en-3-one,
17β-[(2-thienyl)methyl]-4-aza-5α-androst-1-en-3-one,
20-phenyl-4-methyl-4-aza-5α-pregnan-3-one,
20-(4-chloro)phenyl-4-aza-5α-pregnan-3-one,
20-(2-pyridyl)-4-methyl-4-aza-5α-pregn-1-en-3-one,
20-(2-thienyl)-4-aza-5α-pregn-1-en-3-one,
21-phenyl-4-aza-5α-pregnan-3-one,
21-(2-pyridyl)-4-methyl-4-aza-5α-pregnan-3-one,
21-[(4-methoxy)phenyl]-4-methyl-4-aza-5α-pregnan-3-one,
21-(2-thienyl)-4-methyl-4-aza-5α-pregnan-3-one,
21-[(4-chlorophenyl]-4-aza-5α-pregn-1-en-3-one,
4-methyl-17β-[3-(phenyl)propyl]-4-aza-5α-androstan-3-one,
17β-[3-(2-pyridyl)propyl]-4-aza-5α-androst-1-en-3-one,
17β-[3-(4-chlorophenyl)propyl]-4-aza-5α-androstan-3-one,
4-methyl-17β-[2-(thienyl)propyl]-4-aza-5α-androst-1-en-3-one,
4-methyl-17β-[4-(phenyl)butyl]-4-aza-5α-androstan-3-one,
17β-[3-(2-pyridyl)butyl]-4-aza-5α-androst-1-en-3-one,
17β-[3-(4-chlorophenyl)butyl]-4-aza-5α-androstan-3-one,
4-methyl-17β-[2-(thienyl)butyl]-4-aza-5α-androst-1-en-3-one,
20-ethyl-21-(2-pyridyl)-4-aza-5α-pregnan-3-one,
20-ethyl-21-phenyl-4-aza-5α-pregnan-3-one,
20-ethyl-21-(2-methoxyphenyl)-4-aza-5α-pregnan-3-one,
4,21-dimethyl-21-(2-pyridyl)-4-aza-5α-pregnan-3-one,
4,21-dimethyl-21-[(4-benzoylamino)phenyl]-4-aza-5α-pregnan-3-one,
4,21-dimethyl-21-(2-thiazolyl)-4-aza-5α-preganan-3-one,
21-phenyl-4-aza-5α-pregnan-3-one,
21-(2-pyridyl)-4-aza-5α-pregnan-3-one,
21-(2-thienyl)4-aza-5α-pregnan-3-one,
21-(2-methoxyphenyl)-4-aza-5α-pregn-1-en-3-one,
21-(3-pyridyl)-4-aza-5α-pregn-1-en-3-one,
21-(2-thiazolyl)-4-aza-5α-pregn-1-en-3-one,
4-methyl-21-[4-(methylsulfonyl)phenyl]-4-aza-5α-pregn-1-en-3-one,
4-ethyl-21-(4-fluorophenyl)-4-aza-5α-pregn-1-en-3-one,
4-methyl-21-(4-carboxyphenyl)-4-aza-5α-pregn-1,20-dien-3-one,
4-ethyl-21-(4-carbamoylphenyl)-4-aza-5α-pregn-1,20-dien-3-one,
20-(3-pyridyl)-4-aza-5α-pregna-1,17-dien-3-one,
4-methyl-20-(2-pyrazinyl)-4-aza-5α-pregn-1,17-dien-3-one,
20-ethyl-4-methyl-21-phenyl-4-aza-5α-pregn-20-en-3-one,
4,20-dimethyl-21-(2,6-dimethoxyphenyl)-4-aza-5α-pregna-1,20-dien-3-one,
20-ethyl-4-methyl-21-(s-triazinyl)-4-aza-5α-pregna-1,20-dien-3-one,
4-methyl-20-(phenylmethyl)-4-aza-5α-pregnan-3-one,
20-ethyl-4-methyl-21-(2-pyridyl)-4-aza-5α-pregnan-3-one,
20-(2-thiazolyl)-4-aza-5α-pregnan-3-one,
20-ethyl-21-(3-pyridyl)-4-aza-5α-pregnan-3-one,
20-(4-methylsulfonylphenyl)-4-aza-5α-pregn-1-en-3-one,
20-ethyl-21-(4-methoxyphenyl)-4-aza-5α-pregn-1-en-3-one,
4-methyl-20-(3,4-dimethoxyphenyl)-4-aza-5α-pregn-1-en-3-one,
20-ethyl-4-methyl-21-(2-pyrimidinyl)-4-aza-5α-pregn-1-en-3-one,
4,21-dimethyl-21-(4-pyridyl)-4-aza-5α-pregna-1,20-dien-3-one,
21-methyl-21-(2-thienyl)-4-aza-5α-pregn-1-en-3-one,
21-methyl-21-(1-imidazolyl)4-aza-5α-pregnan-3-one,
4,21-dimethyl-21-(4-carbamoylphenyl)-4-aza-5α-pregn-1-en-3-one,
4-methyl-21-(4-methoxyphenyl)-4-aza-5α-pregnan-3-one,
4-methyl-17-((4-chloro)phenylmethyl)4-aza-5α-androstan-3-one,
N-(1,1-dimethylethyl)-4-(4-methyl-3-oxo-4-aza-5α-pregn-21-yl)benzamide,
4-methyl-21-(3-pyridyl)-4-aza-5α-pregn-20-en-3-one, 21-(2-pyrazinyl)-4-methyl-4-aza-5α-preg-20-en-3-one,
4-methyl-21-(2-pyrazinyl)-4-aza-5α-pregnan-3-one,
4-methyl-24-nor-4-aza-5α-cholane-23-nitrile,
4-methyl-3-oxo-4-aza-5α-pregnane-21-carbon-nitrile,
24-nor-4-aza-5α-chol-1-ene-23-nitrile,
24-nor-4-aza-5α-cholane-23-nitrile,
4-methyl-24-nor-4-aza-5α-chol-1-ene-23-nitrile,
3-oxo-4-aza-5α-pregn-1-ene-21-carbonitrile,
3-oxo-4-aza-5α-pregnane-2 1-carbonitrile,
4-methyl-3-oxo-4-aza-5α-pregnane-21-nitrile,
4-methyl-3-oxo-4-aza-5α-cholane-24-nitrile,
3-oxo-4-aza-5α-chol-1-ene-24-nitrile,
4-methyl-3-oxo-21-nor-4-aza-5α-cholane-24-nitrile,
3-oxo-21-nor-4-aza-5α-cholane-24-nitrile,
and also including the corresponding compounds wherein the 4-hydrogen substituent is replaced by a methyl or an ethyl radical, and/or a delta-one double bond is present.

Also included within the scope of this invention are pharmaceutically acceptable salts, i.e. hydrochloride, hydrobromide, acetate, pamoate, and the like, of the compound where a basic heteroaryl radical is present, e.g. 4-pyridyl, which can be used as the dosage form for modifying solubility or hydrolysis characteristics or for use as sustained release or prodrug formulations.

The novel compounds of formula I of the present invention are prepared by methods starting with appropriate steroid 17-carboxaldehydes and ketones of the following formulae:

CHART A

Carboxaldehydes

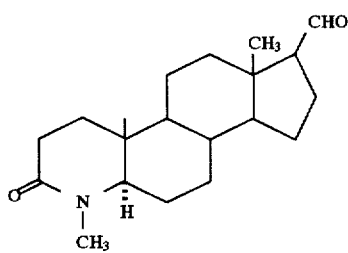

A

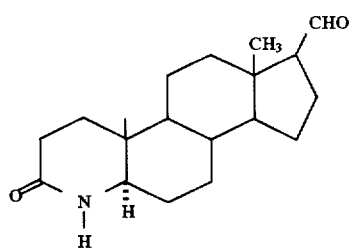

B

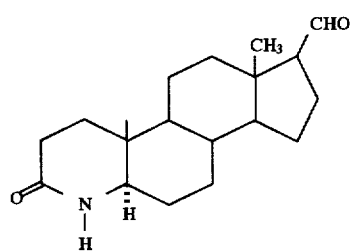

C

-continued
CHART A

Carboxaldehyde A can be prepared from 17-(2-pyridylthio)carboxylate-4-methyl-5α-androstan-3-one by reaction with Raney nickel to the 17β-carbinol followed by oxidation to the aldehyde with pyridinium chlorochromate. (See J. Med. Chem. 1986, Vol. 29, No. 11, p. 2299, Compound 10 bg) The starting 2-pyridylthio ester can be made by hydrolyzing the 17-COOMe derivative to the acid and reacting the acid with 2,2'-dipyridyl disulfide in an inert solvent, e.g. chlorobenzene.

Carboxaldehyde B can be prepared from the lithium aluminum hydride reduction of 17β-(N-methyl-N-methoxy)-carboxamide-5α-4-aza-androst-1-en-3-one (see U.S. Pat. No. 5,061,801 for its preparation, as also described in the following section "Preparation of Starting Materials".

Carboxaldehyde C can be concurrently prepared from the same procedure, as a secondary reaction product, as described above for Carboxaldehyde B (See preparation in "Preparation of Starting Materials").

Note that the corresponding 4-ethyl analogs are also available through conventional alkylation of the 4-NH derivative via, e.g. ethyl iodide, sodium hydride in dry DMF at room temperature.

As seen in Flowsheet A, the carboxaldehydes A, B, or C can be reacted with the phosphonate reagent as shown, where $R^2$ is defined above, $R^3$ is hydrogen or methyl and $R_a$ is a conventional ester alkyl radical, e.g. methyl or ethyl, to yield the Δ-20 olefins IIIa, IIIb & IIIc.

In general, the procedure for reacting the carboxaldehyde with the phosphonate ylid reagent is analogous to the conditions as described for the Wadsworth-Emmons modification of the Wittig reaction (See Chem. Rev. 74, p. 87, 1974 and JACS Vol. 83, p. 1733, 1961). The phosphonate ylid is reacted under anhydrous conditions with the carboxaldehyde in about a 1:1 molar ratio together with a hydride reagent, e.g. sodium hydride, also in a 1:1 molar ratio with the phosphonate reagent in a dry solvent, e.g. dimethylformamide, dimethylacetamide, tetrahydrofuran, dioxane, DMSO and the like, under anhydrous conditions, usually a nitrogen atmosphere, at a temperature of about 50°–100° C., preferably 80°–85° C. for about 14 hours. Workup is conventional, e.g. organic liquid extraction followed by drying, evaporating off solvent, followed by chromatography, distillation or recrystallization of the crude material to yield the desired product, being a species of Formula I.

The starting phosphonates can be prepared by known procedures in the art. One procedure that can be used is the modified Arbuzov reaction in which a chloromethyl-aryl or heteroaryl compound, e.g. thienylmethyl chloride, is reacted with an alkyl phosphite, e.g triethyl phosphite, at 125°–175° C. for 1–10 hours. Conventional workup yields the desired starting phosphonate, e.g. diethyl 2-thienylmethylphosphonate.

FLOWSHEET A
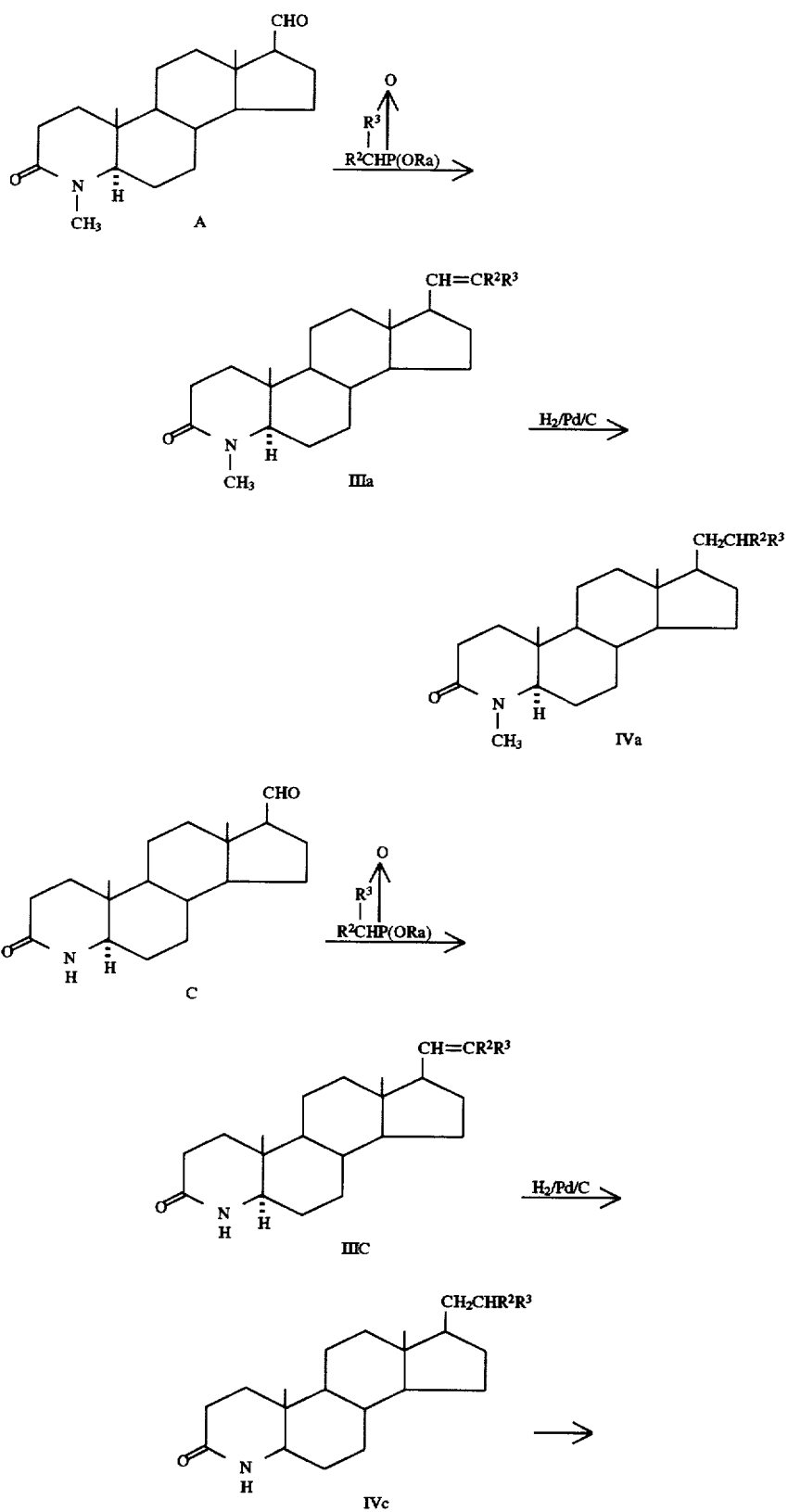

-continued
FLOWSHEET A

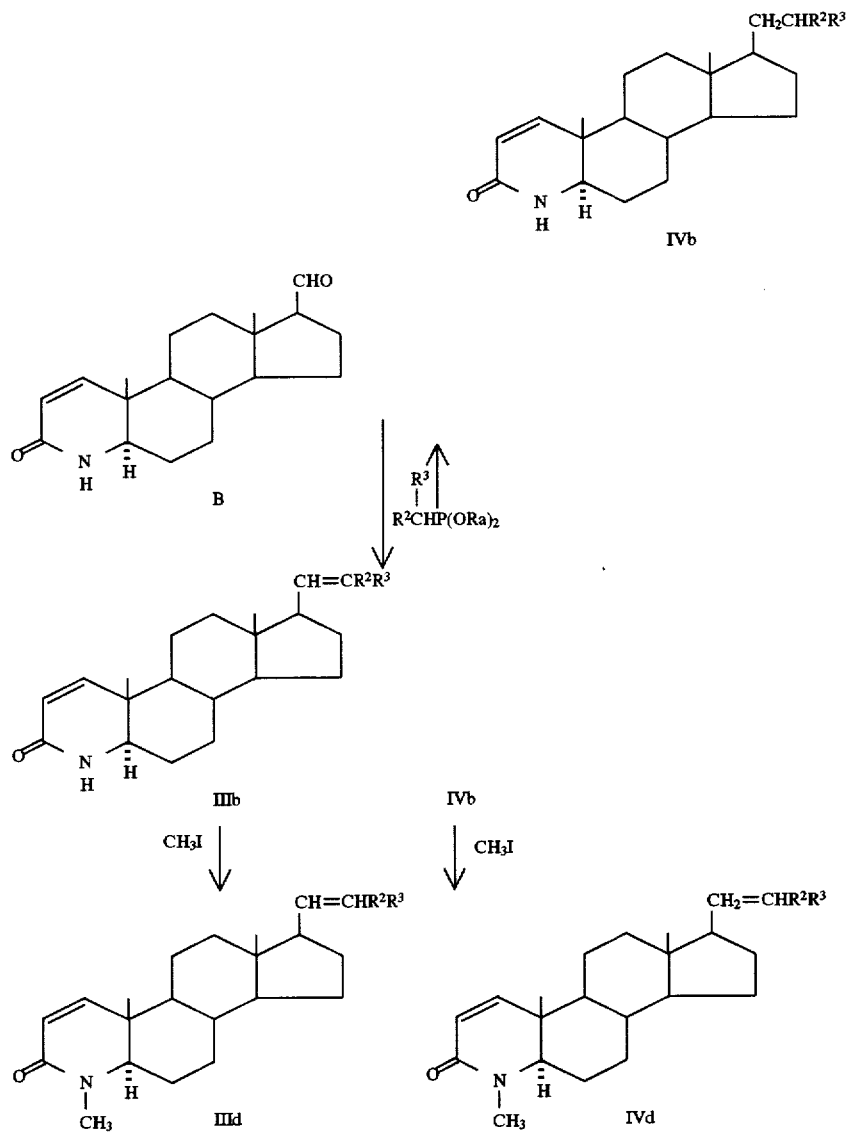

Alternately, the chloromethyl heteroaryl compound, e.g. 4-chloromethylpyridine, can be reacted with diethylphosphite and sodium hydride at about 80°–100° C. for several hours to also produce the desired phosphonate starting materials.

Representative syntheses are given in the "Preparation of Starting Materials" section and representative examples of phosphonate starting materials are:
diethyl 2-thienylmethylphosphonate,
diethyl 4-pyridylmethylphosphonate,
diethyl 4-methylbenzylphosphonate,
diethyl benzylphosphonate,
diethyl 4-chlorobenzylphosphonate,
diethyl 3-chlorobenzylphosphonate,
diethyl 2-chlorobenzylphosphonate,
diethyl 2-pyridylmethylphosphonate,
diethyl 3-thienylmethylphosphonate,
diethyl 2-furanylmethylphosphonate,
diethyl 2-fluorobenzylphosphonate,
diethyl 3-pyridylmethylphosphonate,
diethyl 4-ethoxycarbonylbenzylphosphonate,
diethyl 4-(phenylaminocarbonyl)benzylphosphonate, As outlined on Flowsheet A, the $\Delta^{20}$ olefins IIIa and IIIc can be reduced with e.g. 10% palladium on carbon in a suitable solvent, e.g. methanol, ethanol, dioxane, acetic acid and the like, at room temperature under 1–50 psig hydrogen atmosphere to form IVa and IVc. Compound IVc can be further reacted to form the $\Delta^1$ olefin IVb by the procedure of Dolling et al using dichlorodicyanobenzoquinone, see JACS (1988), Vol 110, pp 3318–3319. Compound 52f (Example 8) was prepared by this procedure. Alternatively IVb can be formed by reacting IVc with benzeneselenic anhydride in refluxing chlorobenzene. The 4-nitrogen in IIIb and IVb can be alkylated with methyl iodide in the presence of sodium hydride in e.g. dry dimethylformamide solvent to give IIId and IVd.

Note that the 4-methyl group in the appropriate compounds in Flowsheet A can be replaced with a 4-ethyl group to prepare the corresponding 4-ethyl analogs of Ea, IVa, IIId, and IVd.

The aldehydes A, B and C can be reacted with diethyl α-methyl-benzylphosphonate (U.S. Pat. No. 4,515,883) in the Wadsworth-Emmons modification of the Wittig reaction and the corresponding products hydrogenated, alkylated on the 4-nitrogen and dehydrogenated as outlined in Flowsheet A to give compounds IIIa–d and IVa–d with $R^2$=phenyl and $R^3$=methyl.

Methyl ketone D (see Chart B) and its preparation is described in J. Med. Chem., 1984, Vol. 27, p. 1690–1701, by G. H. Rasmusson et. al (see Compound 4d.) These compounds can be prepared by reacting the S-(2-pyridyl) androstan-3-one-17β-thio-carboxylate with methylmagnesium chloride under appropriate Grignard conditions.

Methyl Ketone E can be prepared by reacting N-methoxy-N-methyl-3-oxo-4-aza-5α-androst-1-ene-17β-carboxamide (4) with excess methylmagnesium bromide in tetrahydrofuran.

The above 17-methylketones D and E can be reacted with the phosphonate ylids described above in an analogous manner to achieve the 20-methyl pregn-20-en-3-one compounds IIIi and IIIj as illustrated in the following Flowchart B.

FLOWCHART B

-continued
FLOWCHART B

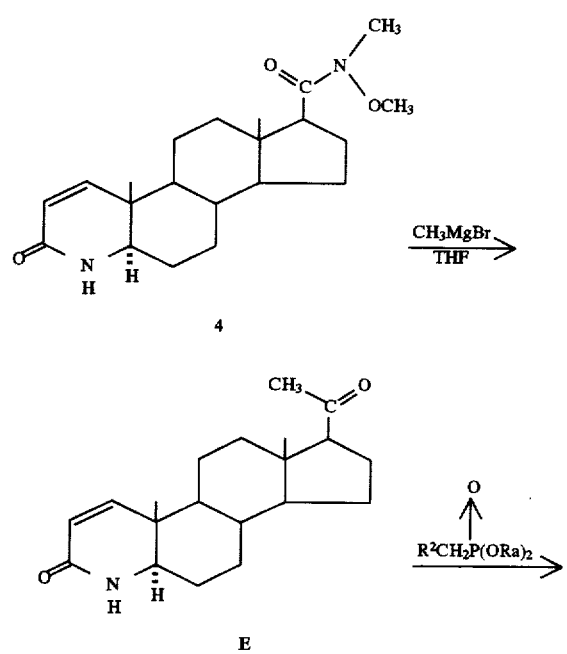

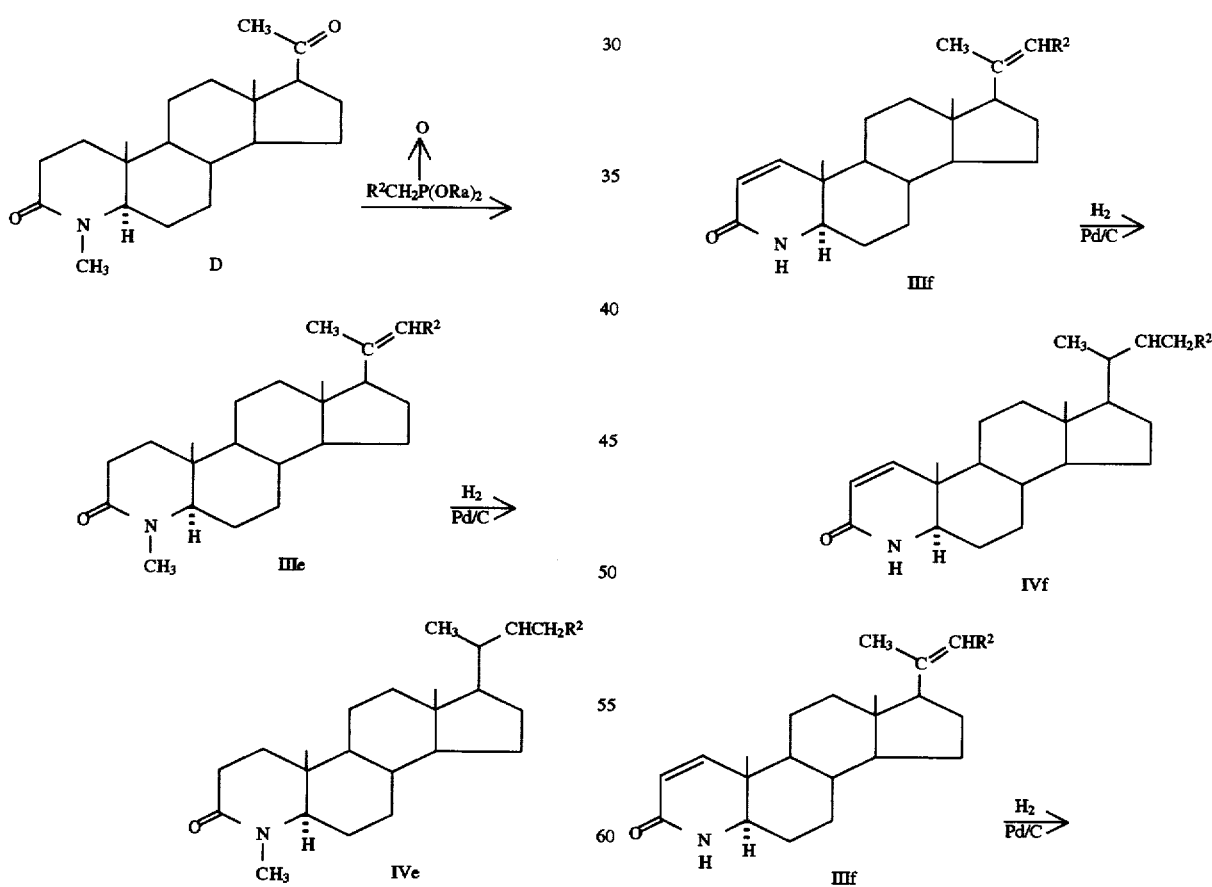

-continued
FLOWCHART B

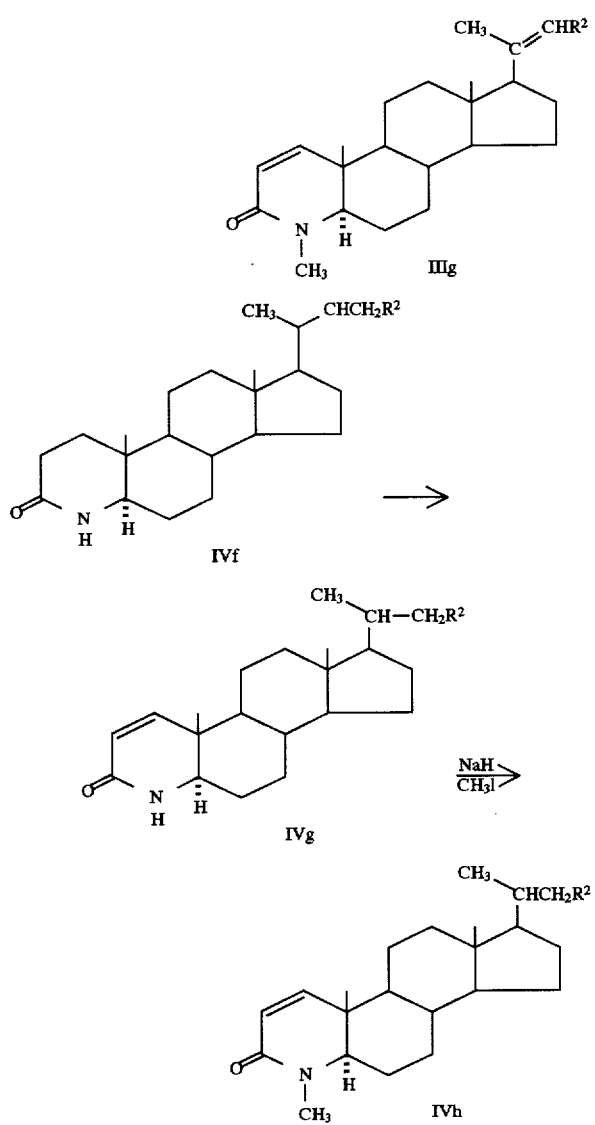

As outlined in Flowsheet B, IIIe and IIIf can be hydrogenated as above to give IVe and IVf. Compound IVf can be dehydrogenated as described above to the Δ'-compound IVg. Compounds IIIf and IVg can be methylated on the 4-nitrogen to give IIIg and IVh.

Also the amide 4 can be reacted with ethyl-magnesium bromide to give ethyl ketone versions of D and E. Using the reactions outlined in Flowsheet B compounds IIIe–g and IVe–h with the 20-methyl replaced by a 20-ethyl can be prepared.

Ketone F (Flowchart C) can be prepared by conventional techniques, including oxidation of the corresponding 17-β-ol with e.g. Jones reagent, and is known in the art in J. Med. Chem. 1984, Vol. 27, p. 1690–1701 by G. H. Rasmusson et. al., (see Compound 22 on p. 1693).

Ketones G and H can be prepared by Jones reagent oxidation of the corresponding 17β-alcohols described in the above reference. Using the reactions shown in Flowsheet A, the ketones F, G, and H are converted into compounds IIIh–k and IVh–l as seen in Flowsheet C.

As indicated in Example 9, the 17β-3-phenylpropyl compound (53) can be prepared from aldehyde A by a phosphonate olefination with diethyl benzoylmethylphosphonate followed by reduction of the ketone and double-bond by hydrogenation with palladium on carbon catalyst in ethanol. Using the reaction sequences outlined in Flowsheet A, the 4-H, Δ'-4-H, and 4-CH₃-Δ' analogs can be prepared starting from aldehydes A or B.

FLOWSHEET B-1

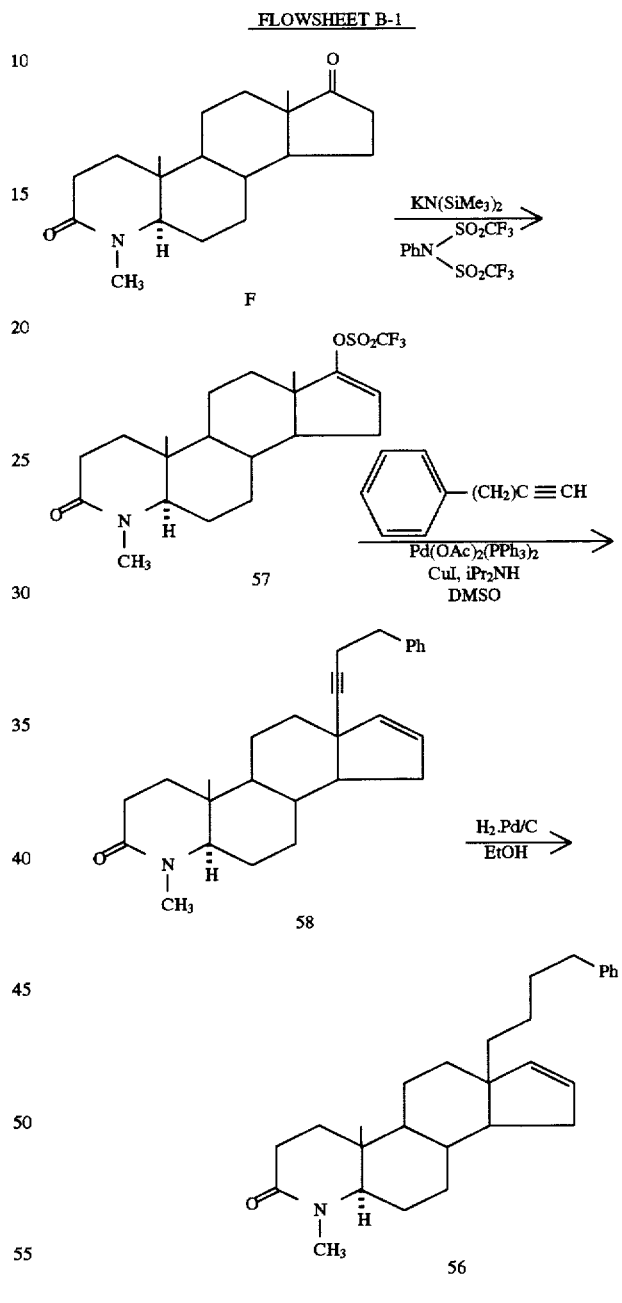

As shown in Flowsheet B-1, the 17β-3-phenyl-butyl compound 56. can be prepared from the ketone F by conversion of the latter to the Δ¹⁶-17-trifluoromethylsulfonate 57 with potassium hexamethyldisilazide and N-phenyltrifluoromethanesulfinimide (*Tetrahedron Lett.* 24, 979 (1983)). Palladium-catalyzed coupling of 57 with 4-phenyl-1-butyne (*Synthesis*, 320 (1986)) can give the en-yne 58 which can be hydrogenated to the desired 17β-3-phenylbutyl compound 56.

FLOWSHEET C
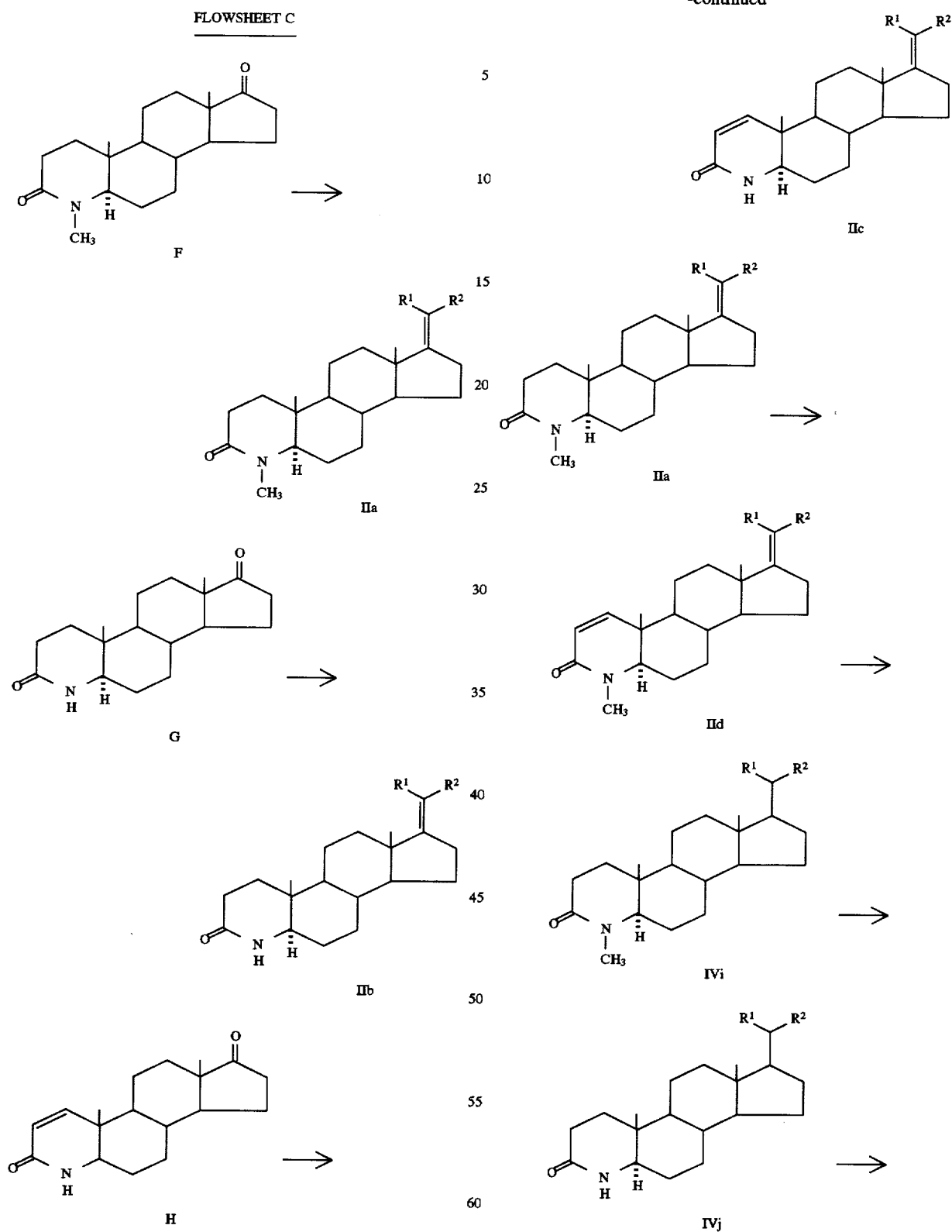

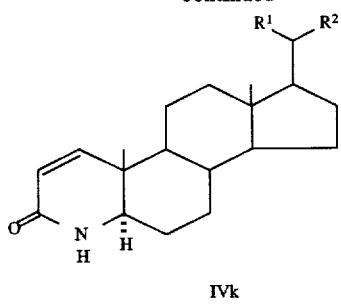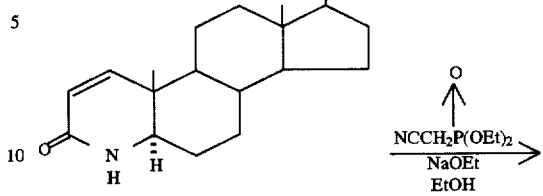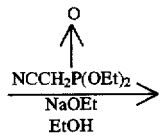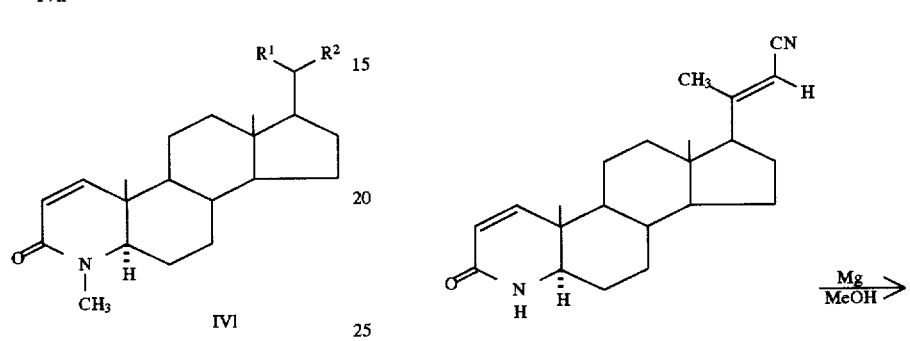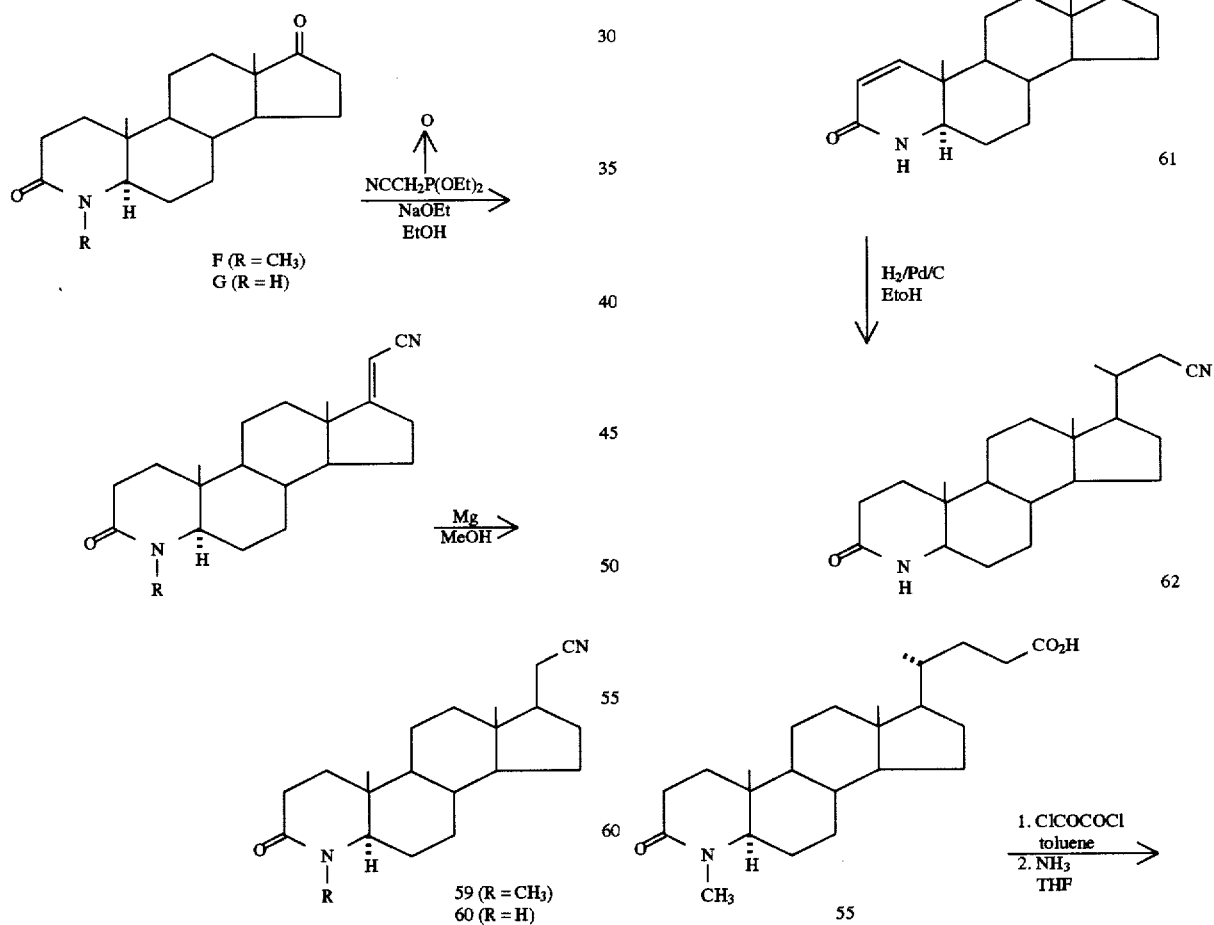

23
-continued

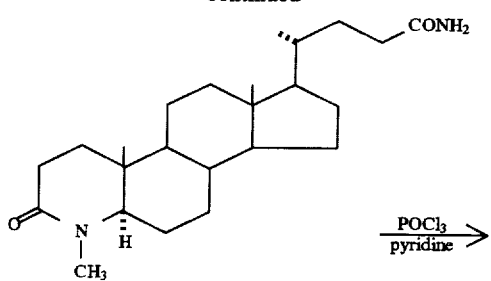

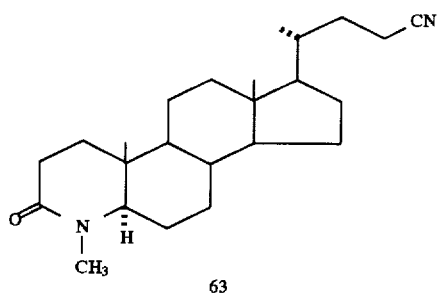

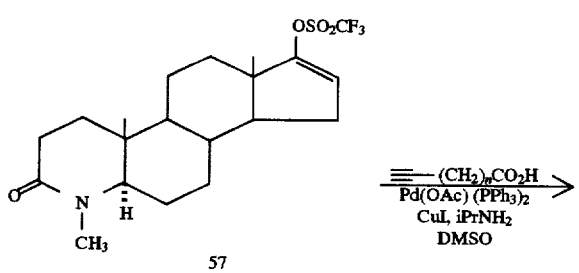

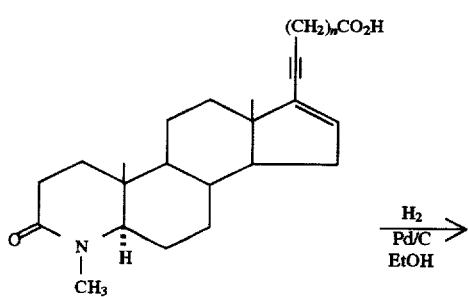

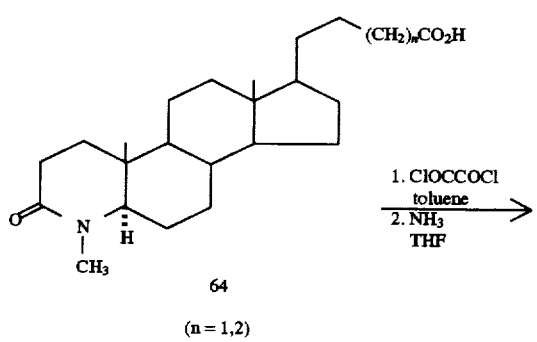

(n = 1,2)

24
-continued

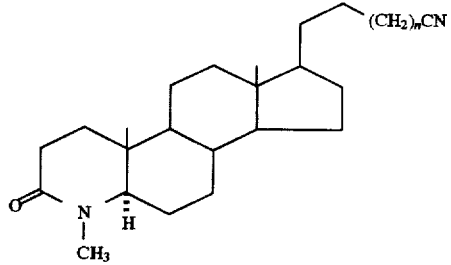

66   (n = 1,2)

As described in Example 10, the nitriles 54 (R=CH₃, H) were prepared from a "second order" Beckmann rearrangement on the homologous carboxylic acids (55, R=CH₃, H) with sodium nitrite in trifluoroacetic acid and trifluoroacetic anhydride. (J. of Lipid Research 29 1387 (1988)).

The synthesis of other nitrites is outlined in Flowsheet D. The pregnane-21-carbonitriles 59 and 60 can be prepared from the ketones F and G by phosphonate olefination with diethyl cyanomethylphosphonate (Steroids 27, 431 (1976)) followed by reduction with magnesium in methanol (J. Org. Chem. 40, 127 (1975)). By the same reaction sequence the ketone E can be converted into the Δ1-4-H-24-nor-cholane-23-nitrile 61 and its reduction product 62. The 24-cholane-24-carbonitrile 63 can be prepared from the cholanic acid 55 by conversion to the primary amide with oxalyl chloride and ammonia followed by dehydration with POCl₃ in pyridine (J. Med. Chem. 29, 2298 (1986)). Similarly the 17-butyric (64, n=1) and valeric (n=2) acids, prepared by palladium-catalyzed coupling of 57 with 3-butynoic and 4-pentynoic acids followed by hydrogenation, can converted into the nitrites 66 (n=1,2).

The method of preparing the novel delta-20-olefinic 4-aza-5α-androstan-3-one compounds of the present invention, already described above in general terms, may be further illustrated by the following examples.

PREPARATION OF STARTING MATERIALS

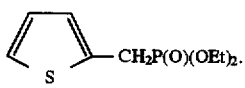   1

A. Preparation of diethyl 2-thienylmethylphosphonate, (1)

Following the general procedure for carrying out the Arbuzov reaction (reference cite: Chem. Rev. 81, 415, 1981) 0.1 mole (17.5 ml) of triethyl phosphite and 0.1 mole (13.2 g) of 2-chloromethylthiophene were combined and heated under $N_2$ at 150° C. for 5 hours. The reaction mixture was cooled and partitioned between 100 ml methylene chloride and 50 ml. water. The organic phase was separated, washed with saturated $NaHCO_3$ solution, dried over magnesium sulfate and concentrated under vacuum to yield 17.5 g. crude liquid product.

The liquid was distilled at 113°–115° C. at 0.5–0.6 mm Hg to yield 5.78 g of the titled product. The proton NMR confirmed the structure of the distilled product.

The following phosphonate reagents were also prepared by the above-described method: diethyl 3-thienylmethylphosphonate, diethyl 2-furanylmethylphosphonate, diethyl 2-fluorobenzylphosphonate, and diethyl 3,4,5-trimethoxybenzylphos-phonate.

B. Preparation of Diethyl 4-Pyridylmethylphosphonate, (2)

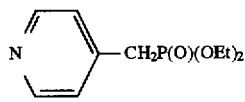

4-Picolyl chloride HCl salt (20 mmol, 3.38 g) was partitioned between 40 milliliters 50% $K_2CO_3$ and 40 milliliters ethyl acetate. The black aqueous phase was extracted (2×) with ethyl acetate and the combined organic phases were dried over magnesium sulfate, and concentrated under reduced pressure. The residue was dissolved in 20 milliliters of toluene.

Sodium hydride (800 mg., 20 mmol) was washed with (3×) hexane and suspended in 8 milliliters of toluene. Diethyl phosphite (5.15 ml, 40 mmol) was added dropwise with stirring and the mixture heated at 80° C. for 30 minutes to yield a clear solution. The toluene solution of the picolyl chloride was added dropwise and the reaction mixture heated at 80° C. for 30 minutes. After cooling, the mixture was poured into water, saturated with sodium chloride, and extracted (3×) with ethyl acetate. The combined organic phases were dried over magnesium sulfate and concentrated under reduced pressure. The liquid residue was distilled under vacuum to yield 2.45 g. (53.5% of theory), b.pt. 123–125/@ 0.3 mm Hg. The proton nmr spectrum confirmed the compound structure.

The following phosphonate reagents were also prepared by the above-described method: diethyl 3-chlorobenzylphosphonate, diethyl 2-chlorobenzylphosphonate, diethyl 2-pyridylmethylphosphonate, diethyl 3-pyridylmethylphosphonate, diethyl 4-pyridylmethylphosphonate, diethyl 4-carbethoxybenzylphosphonate, diethyl 4-(N-phenylcarbamoyl)benzylphosphonate, diethyl pyridazylmethylphosphonate, diethyl 5-thiazolyl-methylphosphonate, diethyl 4-methylsulfonylbenzylphosphonate, and diethyl 2-methoxybenzylphosphonate.

C. Preparation of 4-aza-5α-androst-1-en-3-one-17β-aldehyde (B) and 4-aza-5α-androstan-3-one-17β-aldehyde (C)

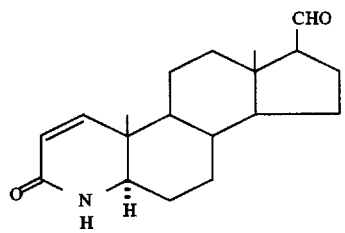

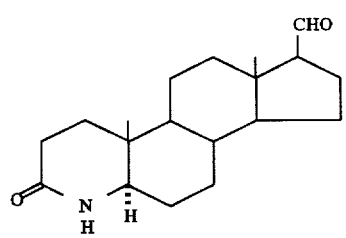

17β-(N-methyl-N-methoxy) carboxamide-5α-4-aza-androst-1-en-3-one (prepared as in following Example D), 3.6 g. (10 mmol) was suspended in 100 ml dry THF at 0° C. under dry nitrogen, lithium aluminum hydride (10 ml of 1M lithium aluminum hydride in dry THF) was added slowly dropwise with stirring maintaining temp at <5° C. After addition was complete the reaction was allowed to stir for 20 minutes. 2N HCl was added to the reaction mixture to pH 3, additional water added and the reaction mixture extracted with (3×) chloroform. The organic phases were combined, dried over magnesium sulfate and concentrated to yield 3.2 g. residue. The crude product was flash chromatographed on a 50 mm.×7" silica gel column with 4:1 methylene chloride/acetone.

The first fractions eluted (12–22) yielded 1.75 g. (58% of the unsaturated aldehyde (B), m.p. 260°–263°.

Fractions (25–36) yielded 0.70 g. (23%) of the saturated aldehyde (C). m.p. 246°–249°.

Proton NMR confirmed the assigned structures for both compounds.

D. Preparation of (5α, 17β)-N-Methoxy-N-methyl-3-oxo-4-aza-androst-1-ene-17β-carboxamide (4)

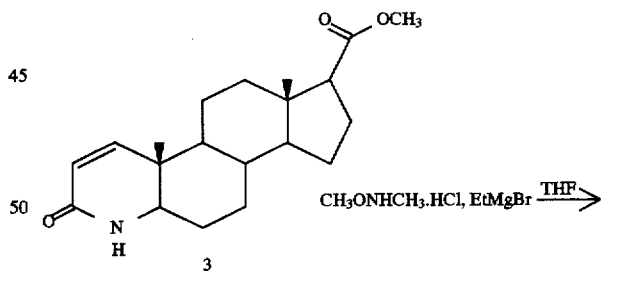

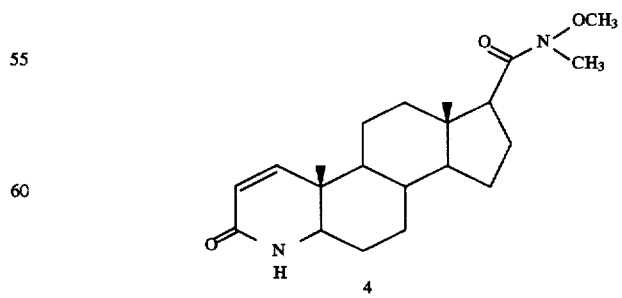

A 2 L three-neck flask equipped with an overhead stirrer, nitrogen inlet, internal thermometer, and/dropping funnel was charged with 800 mL of sieve-dried tetrahydrofuran, 19.72 g (59.6 mmol) of Δ¹-aza ester (Compound 3) (for synthesis, see Rasmusson, Johnston and Arth. U.S. Pat. No. 4,377,584, Mar. 22, 1983.) and 25.6 g (262.4 mmole) of N,O-dimethyl-hydroxylamine hydrochloride. The resulting slurry was cooled to 0° to 5° C.

A warm solution (30°–40° C.) of ethylmagnesium bromide in dry tetrahydrofuran (252 mL, 2.0Molar, 504 mmole) was added over fifteen minutes. The pot temperature was maintained at 0°–5° C. during the addition. The reaction mixture was warmed to 25° C. over thirty minutes and aged at 22°–25° C. for one hour. The reaction was cooled to 0°–5° C. and quenched into 650 mL of 25 wt % aqueous ammonium chloride. The mixture was warmed to 40°–45° C. and the layers were separated. The organic solution was cooled to 25° C. and treated with activated carbon.

The THF solution after filtration was concentrated by atmospheric distillation to 200 mL. The resulting slurry was cooled to 35° C. and 1 L of water was added over one hour. The slurry was cooled to 25° C. and aged for 2 hours. The amide was collected by filtration and washed with 200 mL of water then dried at 80° C./house vacuum to yield 19.6 g (91.4%) of amide 4 (98.8 area % pure by LC).

E. Preparation of 4-aza-5α-pregn-1-ene-3,20-dione (E)

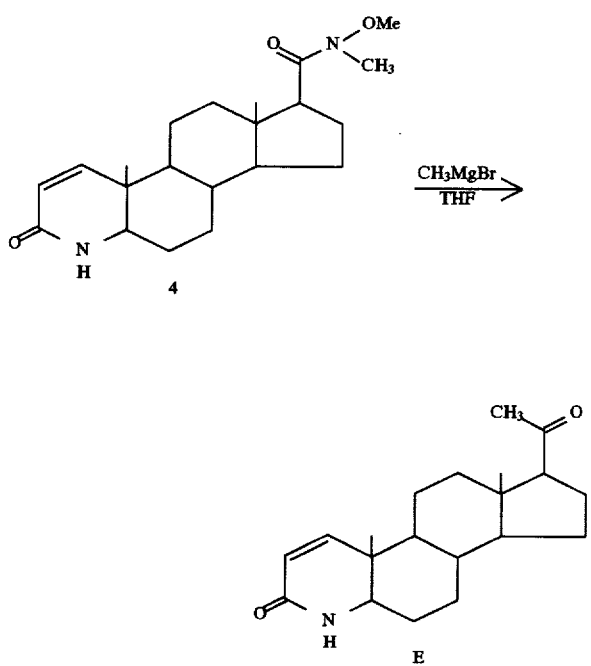

To a slurry of 4 (12 g, 33 mmoles) in 480 ml of dry tetrahydrofuran was added dropwise 83.3 ml (250 mmoles) of 3.0M methylmagnesium bromide in diethyl ether while maintaining the temperature of the reaction <5° with cooling with an ice bath. The mixture was stirred at room temperature for 8 hours. After cooling in an ice bath, 500 ml of aqueous ammonium chloride (1 g/3 ml H₂O) was added. Most of the tetrahydrofuran was removed in vacuo. The slurry was filtered, and the solid washed with H₂O, dried, triturated with Et₂O, filtered and dried to give 10.5 g of 4-aza-5α-pregn-1-ene-3,20-dione, mp. 310°–312°. The NMR spectrum confirmed the assigned structure.

EXAMPLE 1

REACTION OF 17-CARBOXALDEHYDE WITH PHOSPHONATE REAGENT

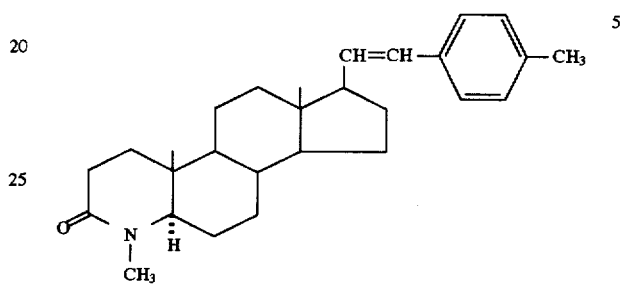

1. Preparation of 17β-(1-(2-(4-tolyl))ethenyl)-4-methyl-4-aza-5α-androstan-3-one, (5).

Following the general procedure of Wadsworth, et al., (see Chem. Rev. 74, 87 (1974) and JACS, Vol. 83, p. 1733 (1961), 5-alpha-4-aza-4-methyl-androstan-3-one-17-aldehyde, Carboxaldehyde A, (245 mg, 0.77 mol), sodium hydride (31 mg, 0.78 mol), diethyl 4-methylbenzylphosphonate (189 mg., 0.78 mol) in 2 ml. anhydrous dimethylformamide was stirred at 80° C. in a nitrogen atmosphere for 1.5 hours. The reaction was cooled and partitioned with 20 ml. each of 0.1N HCl/methylene chloride. The organic phase was washed with water, dried over magnesium sulfate and concentrated under reduced pressure to yield 391 mg. crude solid. Recrystallization from ethyl acetate yielded a white solid, mp 225°–227° C. The proton NMR and mass spectrum confirmed the assigned structure for 5.

EXAMPLE 2

Following the general procedure described above in Example 1, the following tabulated compounds were prepared.

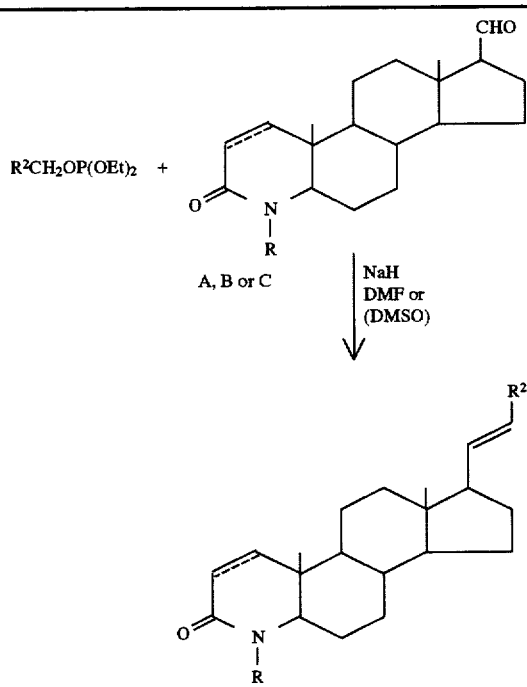

IIIa, b; c.

| Structure | Compound No. | R | R² | Mass Spec. method: | m/e | TLC solvent system | $R_f$ |
|---|---|---|---|---|---|---|---|
| IIIa | 6 | Me | 4-methoxyphenyl | EI | 421 | A | 0.4 |
| " | 7 | Me | phenyl | EI | 391 | B | 0.5 |
| " | 8 | Me | 4-tolyl | EI | 405 | B | 0.4 |
| " | 9 | Me | 4-chlorophenyl | EI | 425 | B | 0.5 |
| " | 10 | Me | 4-pyridyl | EI | 392 | C | 0.25 |
| " | 11 | Me | 3-chlorophenyl | EI | 425 | B | 0.5 |
| " | 12 | Me | 2-chlorophenyl | EI | 425 | B | 0.5 |
| " | 13 | Me | 2-pyridyl | EI | 392 | C | 0.3 |
| " | 14 | Me | 2-thienyl | EI | 397 | B | 0.5 |
| IIIc | 15 | H | 4-methoxyphenyl | EI | 407 | C | 0.5 |
| IIIa | 16 | Me | 3-thienyl | Ei | 397 | B | 0.4 |
| " | 17 | Me | 2-furanyl | EI | 381 | B | 0.4 |
| " | 18 | Me | 2-fluorophenyl | EI | 409 | B | 0.4 |
| IIIb | 19 | H* | 4-pyridyl | EI | 376 | C | 0.3 |
| IIIc | 20 | H | 4-pyridyl | EI | 378 | D | 0.3 |
| IIIb | 21 | H* | 4-methoxyphenyl | EI | 405 | C | 0.5 |
| " | 22 | H* | 2-furanyl | EI | 365 | C | 0.5 |
| " | 23 | H* | 2-pyridyl | EI | 376 | C | 0.3 |
| " | 24 | H* | 3-pyridyl | FB' | 377 | C | 0.3 |
| " | 25 | H* | 4-ethoxycarbonyl phenyl | FB' | 447 | C | 0.4 |
| " | 26 | H* | 4(N-phenylcar-bamoyl)phenyl | FB' | 495 | E | 0.7 |
| IIIc | 27 | H | 2-pyridyl | EB" | 380 | C | 0.2 |
| " | 28 | H | 3-pyridyl | EI | 378 | F | 0.3 |
| " | 29 | H | 2-thienyl | FB' | 384 | C | 0.2 |
| IIIa | 29a | Me | 3,4,5-trimethoxy-phenyl | EI | 481 | C | 0.5 |
| " | 29b | Me | pyrazinyl | EI | 393 | C | 0.3 |
| " | 29c | Me | 3-pyridyl | EI | 392 | C | 0.4 |
| IIIb | 29d | H* | pyrazinyl | EI | 377 | C | 0.4 |
| " | 29e | H* | 5-thiazolyl | EI | 382 | C | 0.4 |
| " | 29f | H* | 4-methylsulfonyl-phenyl | FB' | 454 | C | 0.5 |
| " | 29g | H* | 2-methoxyphenyl | FB' | 406 | C | 0.6 |
| " | 29h | H* | 4-(N-(4-pyridyl) carbamoylphenyl | EI | 495 | G | 0.4 |

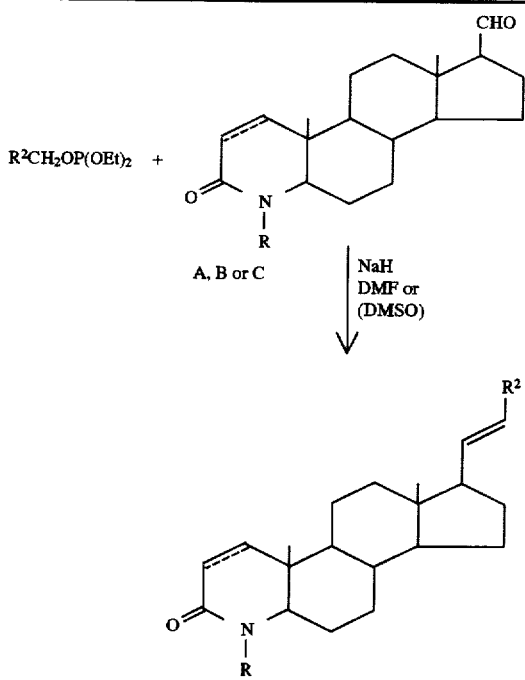

| | Compound | | | Mass Spec. | | TLC solvent | |
|---|---|---|---|---|---|---|---|
| Structure | No. | R | $R^2$ | method: | m/e | system | $R_f$ |
| " | 29i | H* | 4-(N-methyl-N-(4-pyridyl)carbamoyl)-phenyl | E.I | 509 | G | 0.5 |

Note: in the above table the TLC symbols used are-indicated as:
A - ethyl acetate
B - 4:1 ethyl acetate/hexane
C - 4:1 methylene chloride/acetone
D - 3% methanol/methylene chloride
E - 1:1 methylene chloride/acetone
F - 7:3 methylene chloride:acetone
G - 5% methanol/methylene chloride The mass spectral data were obtained by either electron impact (EI) or fast atom bombardment (FB) techniques.

The FB recorded results with one prime, $FB^1$, indicates m+1; with two primes, $FB^{11}$, indicates m+2. Also, the asterisk denotes the presence of the 1,2-double bond ($\Delta^1$). The starting materials used were the aldehyde, A, for the 4-N-methyl derivatives; C, for 4-NH derivatives; and B, for the 1-ene-4-NH derivatives.

EXAMPLE 3

REACTION OF 17-METHYL KETONES WITH PHOSPHONATE REAGENT

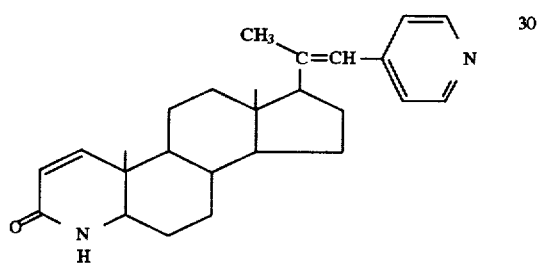

33

Preparation of: (20E)-20-methyl-21-(4-pyridyl)-4-aza-5α-pregn-1,20-dien-3-one, (30)

Following the general procedure of Wadsworth et al.; cited above, to a solution of 4-aza-5α-pregn-1-ene-3,20-dione (E) (158 mg., 0.5 mmol) and 229 mg (1.0 mol) diethyl 4-pyridylmethylphosphonate in 2 ml. anhydrous DMSO, was added all at once under $N_2$ atmosphere, 50 mg. (1.25 mmol) of sodium hydride (60%). The reaction mixture was stirred and heated at 85° C. under a $N_2$ atmosphere for 3 hours. Hydrogen evolution stopped after 15 minutes. The dark reaction mixture was cooled, poured into 30 ml $H_2O$ and extracted (3×) with methylene chloride. The combined organic phase was washed with water, dried over magnesium sulfate and concentrated under reduced pressure to yield a brown gum. The crude material was chromatographed on silica gel plates with 1:1 methylene chloride/acetone and the strong UV active band was eluted 2:1 methylene chloride/methanol. The eluate was concentrated to yield pure product after trituration with ether, mp 268°–270° C. (dec.). The proton NMR comfirmed the assigned structure for 30.

EXAMPLE 4

Following the general procedure of Example 3, the following tabulated compounds were prepared.

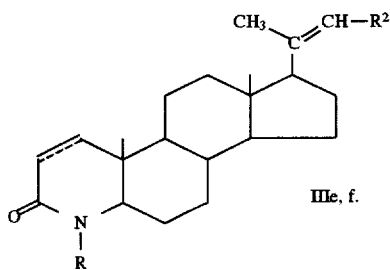

IIIe, f.

TABLE 2

| Structure | Compound No. | R | R² | Physical Properties |
|---|---|---|---|---|
| IIIe | 31 | Me | Phenyl | NMR* |
| IIIe | 32 | Me | 4-chlorophenyl | mp. 208–211° C. |
| IIIe | 33 | Me | 2-thienyl | mp. 220–222° C. |
| IIIe | 34 | Me | 2-pyridyl | mp. 200–203° C. |
| IIIf | 35 | H* | 4-pyridyl | mp. 268–278° C. (dec.) |
| IIIe | 36 | Me | 4-pyridyl | NMR** |
| IIIf | 37 | H* | 2-furyl | mp. 290–294° C. (dec.) |
| IIIf | 38 | H* | 2-pyridyl | mp. 255–258° C. (dec.) |

*NMR(CDCl₃)δ 0.65 (S, 3H, 18-Me), 0.90 (S, 3H, 19-Me), 1.88 (S, 3H, 21-Me), 2.94 (S, 3H, N—Me), 6.35 (bs, 1H C=CH—), 7.1–7.4 (m, 5H, ArH).
**NMR(CDCl₃)δ 0.65 (S, 3H, 18-Me), 0.91 (S, 3H, 19-Me), 1.92 (S, 3H, 21-Me), 2.94 (S, 3H, N—Me), 6.25 (bs, 1H, C=CH—), 7.19 (vbs, 2H, pyridyl H), 8.6 (vbs, 2H, pyridyl H).

34

EXAMPLE 5

REACTION OF PHOSPHONATE REAGENTS WITH 17-KETO ANDROSTANES

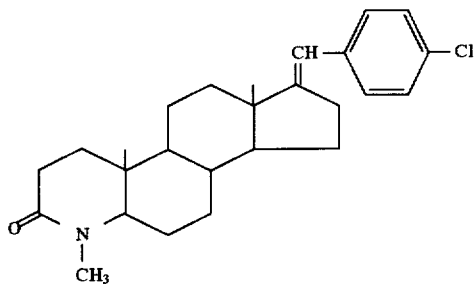

Preparation of 17-[(2-chlorophenyl)methylene]-4-methyl-5α-androstan-3-one, (39)

Sodium hydride (60%, 26 mg, 0.66 mmole) was added to a solution of 101 mg. (0.33 mol) of 17-keto-4-methyl-5α-androstan-3-one (F) and 173 mg (0.66 mol) of diethyl 2-chlorobenzylphosphonate in 1.0 ml of dry DMF at room temperature. The mixture was heated at 70° C. in a nitrogen atmosphere with stirring for 110 minutes, cooled, poured into 0.5N HCl (20 ml) and extracted with methylene chloride (3×). The organic phases were combined, washed with water (3×), saturated NaCl solution and dried over magnesium sulfate. The organic phase was concentrated under reduced pressure to yield a tan, gummy solid. Flash chromatography of the crude solid was conducted on a silica gel 60×20 mm column, and eluted with 4:1 methylene chloride/acetone in 6 ml. fractions. Fractions 18–24 contained the product which were combined and evaporated to yield a white solid, mp 205°–208° C., yielding one spot on silica gel TLC using 4:1 methylene chloride/acetone. The proton NMR confirmed the assigned structure for 39.

EXAMPLE 6

Following the general procedure of Example 5 but using different phosphonate reactants, the following compounds were prepared as listed in the following Table 3.

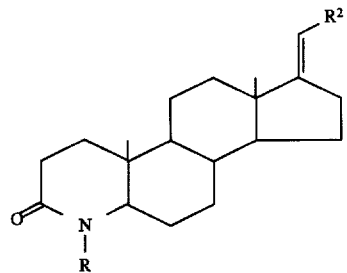

TABLE 3

| No. | R | R² | Physical Properties |
|---|---|---|---|
| 40 | Me | phenyl | mp. 193–197° C. |
| 41 | Me | 4-chlorophenyl | mp. 138–141° C. |
| 42 | Me | 3-chlorophenyl | mp. 236–240° C. |
| 43 | Me | 2-chlorophenyl | mp. 205–208° C. |
| 44 | Me | 4-ethoxycarbonylphenyl | mp. 178–182° C. |
| 45 | Me | 4-carboxyphenyl | mp. >330° C. |

TABLE 3-continued

| No. | R | $R^2$ | Physical Properties |
|---|---|---|---|
| 46 | Me | 4-(t-butyl)amino-carbonylphenyl | NMR* |

*NMR(CDCl$_3$)δ  0.86 (S, 3H, 18-Me), 0.90 (S, 3H, 19-Me), 1.45 (S, 9H, CMe3), 2.92 (S, 3H, N—Me), 5.92 (bs, 1H, NH), 6.05 (t, 1H, C=CH—), 7.32 (d, J = 8 Hz, 2H, ArH), 7.65 (d, J = 8 Hz, 2H, ArH).

EXAMPLE 7

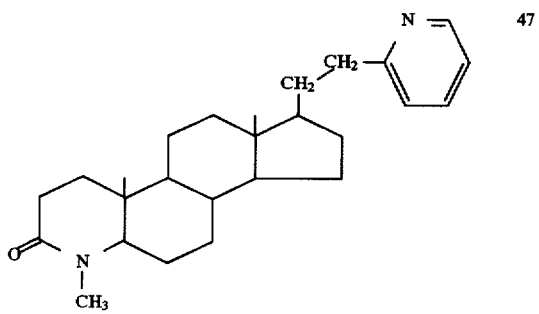

47

CATALYTIC REDUCTION OF DELTA-17 and -20 OLEFINS

Preparation of 21-(2-pyridyl)-4-dimethyl-4-aza-5α-pregnan-3-one. (47)

A mixture of 0.075 g. (0.191 mmol) of (20E)-4,20-dimethyl-21-(2-pyridyl)-4-aza-5α-pregn-20-en-3-one, 0.075 mg 10% Pd/C catalyst in 3 ml ethanol were hydrogenated at room temperature under a 45 psig hydrogen atmosphere with shaking for 45 minutes. The reaction mixture was filtered through Celite and concentrated to yield 74 mg of product. The crude solid was chromatographed on a 2000 micron silica gel plate in 4:1 methylene chloride/acetone. The product was eluted using 5% MeOH/methylene chloride and concentrated to yield product 21-(2-pyridyl)-4-methyl-4-aza-5α-pregnan-3-one. The assigned structure for 41 was confirmed by proton NMR. Fast atom bombardment mass spectrum also confirmed a molecular ion peak of M+2=396, and the Rf value on silica gel in 4:1 methylene chloride eluant was 0.2.

EXAMPLE 8

Following the general procedure of Example 7, the following saturated compounds were prepared from the corresponding $\Delta^{17}$ or $\Delta^{20}$ olefin, or $\Delta^{16,20}$ diene (See Example 11):

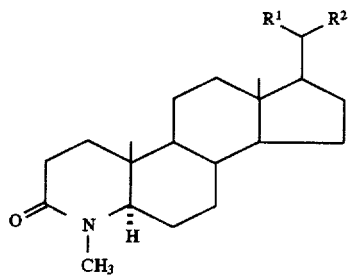

| Structure | No. | $R^1$ | $R^2$ | Physical Properties |
|---|---|---|---|---|
| IVa $R^2$=H | 48 | H | CH$_2$—⟨phenyl⟩—OCH$_3$ | M$^+$423 m/e (EI); R$_f$ 0.4 EtOAc |
| IVc R=H | 49 | H | ⟨phenyl⟩—Cl | * |
| IVa $R^2$=H | 50 | H | CH$_2$—⟨thienyl, S⟩ | M + 1 400 m/e (FAB); R$_f$ 0.6 CH$_2$Cl$_2$—acetone (4:1) |
| IVa $R^2$=H | 51 | H | CH$_2$—⟨phenyl⟩—CONH— | ** |

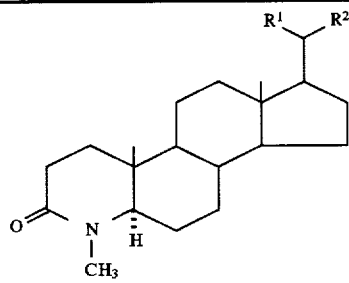

| Structure | No. | R¹ | R² | Physical Properties |
|---|---|---|---|---|
| IVe R=Me | 52 | CH₃ | CH₂—⌬ | *** |

*NMR (CDCl₃) δ 0.69 (s, 3H, 18-Me), 0.89 (s, 3H, 19-Me), 2.92 (s, 3H, N—Me), 7.08 (d, 2H, ArH), 7.22 (d, 2H, ArH).
**NMR (CDCl₃) δ 0.59 (s, 3H, 18-Me), 0.75 (s, 3H, 19-Me), 1.44 (s, 9H, CMe₃), 2.91 (s, 3H, N—Me), 5.90 (bs, 1H, NH), 7.19 (d, 2H, ArH), 7.61 (d, 2H, ArH).
***NMR (CDCl₃) δ 0.68, 0.70, 0.78, 0.80, 0.84, 0.86, 0.91, 0.92 (s, 9H, 2 sets of 18- and 19-Me and 2(two) 21-Me doublets), 2.93 (s, 3H, N—Me), 7.1–7.3 (m, 5H, ArH).

EXAMPLE 9

Preparation of 4-Methyl-17β-[3-(phenyl)propyl]-4-aza-5α-androstan-3-one (53)

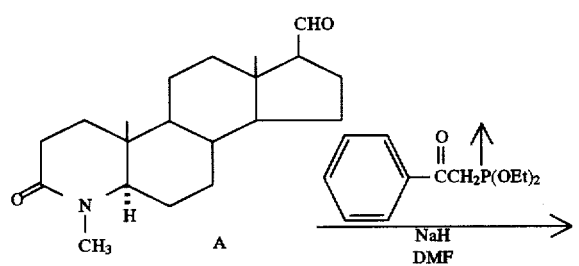

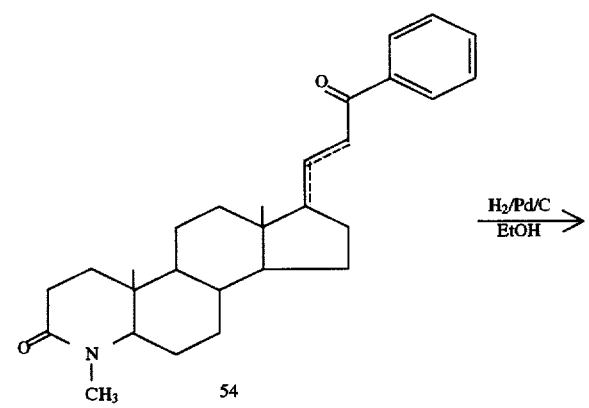

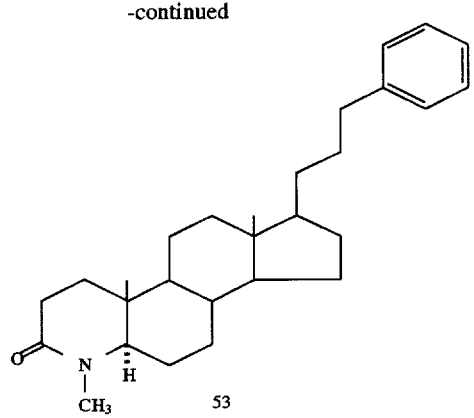

To a solution of 225 mg (0.71 mmoles) of aldehyde A and 185 mg (0.72 mmoles) of diethyl benzoylmethylphosphonate in 2 ml of DMF was added 29 mg (0.72 mmoles) of sodium hydride (60%) and the mixture heated at 80° in a N₂ atmosphere for 1 hour. The cooled reaction was poured into H₂O (50 ml) and extracted with CH₂Cl₂ (3×). The combined extracts were washed with water and brine and dried with magnesium sulfate. Evaporation in vacuo gave an oily solid, which was flash chromatographed on a 20m×7" silica gel column with 7:3 ethyl acetate-hexane taking 18 ml fractions. Evaporation of fractions 25–42 gave 160 mg of a solid. NMR and TLC indicated it was a 1:1 mixture of $\Delta^{17}$ and $\Delta^{20}$ olefin isomers (54).

A 60 mg sample of 54 was hydrogenated with 50 mg of 10% palladium on carbon in 3 ml of ethanol at 40 psi for 5 hours. The reaction was filtered through a bed of Celite, and the solid washed with ethanol (3×). The filtrated was evaporated in vacuo to give pure 53. Mass spectrum: m/e 408 (M+1) (FAB) R_f 0.35 EtOAc-hexane (4:1).

EXAMPLE 10

Preparation of 4-Methyl-24-nor-4-aza-5α-cholane-23-nitrile (54) (R=CH₃)

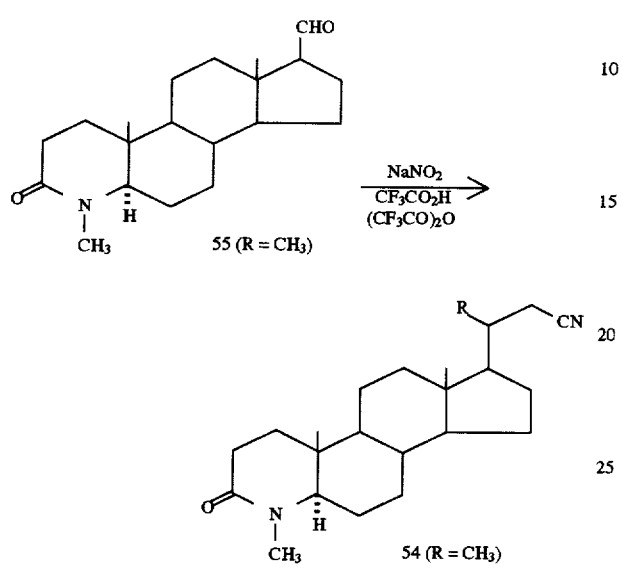

To a solution of 470 mg (1.18 mmoles) of 4-methyl-3-oxo-4-aza-5α-cholan-24-oic acid [G. H. Rasmusson, et al. J. Med. Chem. 1986, 29, 2298 (1986)] in 2.0 ml of trifluoroacetic acid and 0.52 ml of trifluoroacetic anhydride, cooled to 0° C., was added all at once 92 mg (1.33 mmoles) of sodium nitrite. After stirring at 0° for 45 min, the reaction was placed in a 40° oil bath. There was copious evolution of nitrogen, and the reaction darkened. After 20 minutes, the reaction was poured into 2 ml of 2N NaOH and 16 g of ice, extracted with CH₂Cl₂ (4×). The extracts were washed with H₂O and dried with magnesium sulfate. Evaporation in vacuo gave 195 mg of a tan solid. Flash chromatography on a 20 mm×7" column of silica gel with 6:1 CH₂Cl₂-acetone taking 10 ml fractions. Evaporation in vacuo of fractions 13–30 gave pure 54, m.p. 211°–214°. The NMR spectrum confirmed the assigned structure.

Using the same procedure, 4-methyl-3-oxo-21-nor-4-aza-5α-cholan-24-oic acid (55, R=H) gave 4-methyl-3-oxo-4-aza-5α-pregnane-21-carbonitrile (54, R=H) Mass spectrum: M+342 m/e; Rf 0.5 CH2Cl2-acetone (4:1).

EXAMPLE 11

21-(1-Phenyltetrazol-5-yl)-4-aza-4-methyl-5a-prepgnan-3-one (52c)

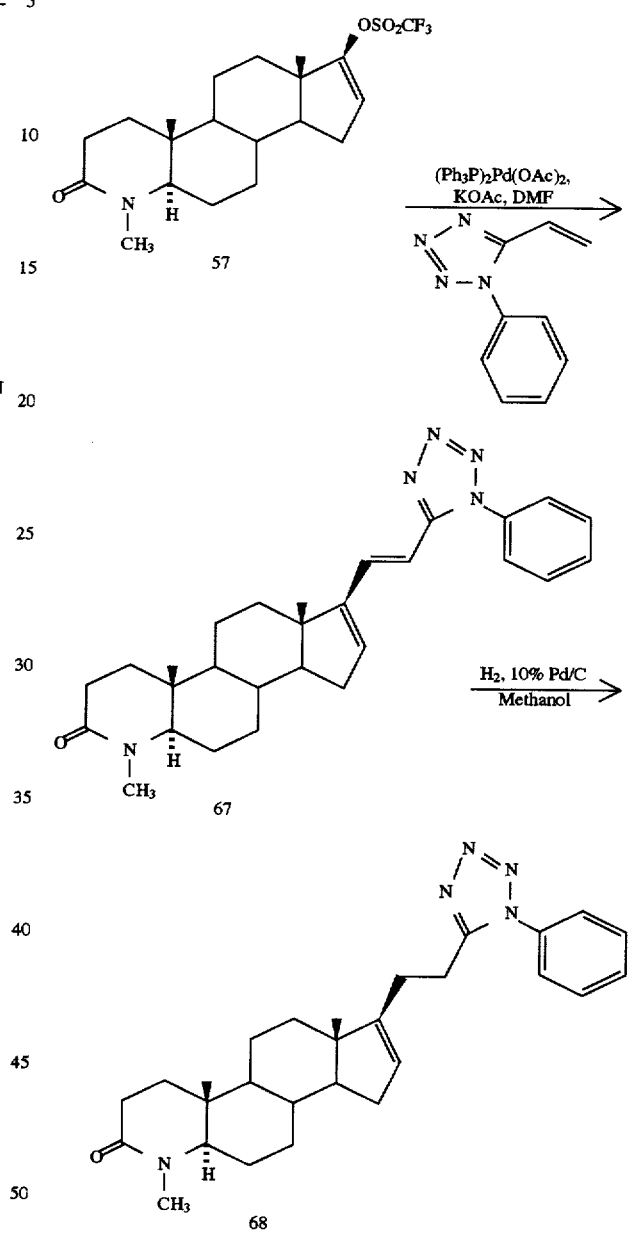

To a solution of the triflate (57) (131 mg, 0.3 mmole) in 3 ml of dry DMF under N2 was added 5-vinyl-1-phenyltetrazole (207 mg, 1.2 mmole), bis(triphenylphosphine)palladium(II) acetate (22 mg, 0.03 mmole), and potassium acetate (118 mg, 1.2 mmole) and the reaction mix stirred at 80° C. for 2 hours The mixture was cooled to room temperature and partitioned with methylene chloride—water. The organic phase was washed with water, brine, dried over magnesium sulfate, filtered and concentrated in vacuo to give 305 mg of crude product. Purification by flash chromatography on silica gel in 7:1 methylene chloride:acetone gave 64 mg of the bis olefin (67).

To a solution of the bis olefin (67) in 2 ml of methanol was added 30 mg of 10% Palladium on activated carbon and the mixture stirred under a balloon of hydrogen for 6 hours at room temperature. The mixture was filtered through Celite washing with methanol and the filtrate was concentrated in vacuo to give 63 mg of crude product. Purification by preparative thin layer chromatography on silica gel in 4:1 ethyl acetate:hexane (running the solvent mix up the plate 2 times) gave 30 mg of the reduced phenyl tetrazole (52c).

Compounds 52b, 52d, and 52e were prepared by the same procedure.

Also included with the scope of this invention are 4-N-X analogs where X is OH, $NH_2$ or $SCH_3$. The 4-N-OH and 4-N-$NH_2$ derivatives can be made by incorporating hydroxylamine or hydrazine, respectively, in place of methylamine in the seco acid ring A closure for the starting androstanes herein as described in J. Med. Chem. 29, 2998–2315 (1986) by Rasmusson, et al. Further, reaction of the anion of the saturated 4-N-H androstanes, wherein the anion is generated from the 4-NH precursor by sodium hydride, and methylsulfenyl chloride can product the corresponding 4-N-S-$CH_3$ derivative. Thus, Substituent R on the 4N-position also includes CH, $NH_2$ and 5-$CH_3$.

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. For the treatment of androgenic alopecia, acne vulgaris, seborrhea, female hirsutism, the compounds of the present invention are administered in a pharmaceutical composition comprising the. active compound in combination with a pharmacologically acceptable carrier adapted for topical, oral or parenteral administration.

These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a 5α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range between about Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

BIOLOGICAL ASSAYS

Preparation of Human prostatic and scalp 5a-reductases.

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min.

The crude nuclear pellet was washed two times and resuspended in two volumes of buffer. Glycerol was added to the resuspended pellet to a fmal concentration of 20%. The enzyme suspension was frozen in aliquots at −80° C. The prostatic and scalp reductases were stable for at least 4 months when stored under these conditions.

5α-reductase assay.

The reaction mixture contained in a final volume of 100 µl is: 40 mM buffer (human scalp, potassium phosphate, pH 6.5; human prostatic 5α-reductase, sodium citrate, pH 5.5), 0.3–10 µM $^{14}$C-T (or $^{3}$H-T), 1 mM DTT, and 500 µM NADPH. Typically, the assay was initiated by the addition of 50–100 µg prostatic homogenate or 75–200 µg scalp homogenate and incubated at 37° C. After 10–50 min the reaction was quenched by extraction with 250 µl of a mixture of 70% cyclohexane: 30% ethyl acetate containing 10 µg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times DHT, 6.8–7.2 min; androstanediol, 7.6–8.0; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radio-activity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Stumptail macaque protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:
1. Topical 50:30:20 vehicle (N=6)
2. Oral 5α-reductase and topical 50:30:20 vehicle (N=5)
3. Oral placebo (N=5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tatoos) in the center of the balding scalp. This hair collection is the baseline hair growth determination prior to the beginning of treatment. Approximately 250 µL of vehicle and 5α-reductase in vehicle is prepared and topically administered to the tatooed area of the scelp. The selected 5α-reductase and placebo is ingested by the monkeys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the nonparametric Wilcoxon rank-sum test. Differences are significant at p<0.05. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula:

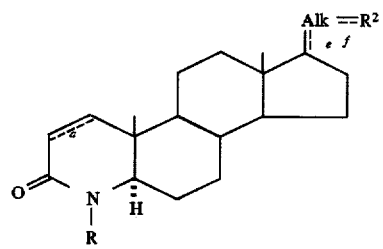

wherein:

Alk is $C_1$–$C_4$ straight or branched chain alkyl or alkenyl; dashed lines a, e and f each can independently represent a double bond when present, with the proviso that double bonds formed by e and f are not both present concurrently;

R is hydrogen, methyl or ethyl;

$R^2$ is
(b) $COR^{11}$ wherein $R^{11}$ is $C_6-C_{10}$ aryl, or substituted $C_6-C_{10}$ aryl;
(c) $CONHR_{12}$, where $R_{12}$ is substituted phenyl; providing that in (b), or (c), Alk is alkenyl;

wherein $C_6-C_{10}$ aryl is selected from phenyl and naphthyl; wherein said substituted aryl groups are substituted with a substituent selected from:

hydrogen;
$C_{1-8}$ straight or branched alkyl;
$C_{2-8}$ straight or branched alkenyl;
$C_{3-8}$ cycloalkyl;
$C_{2-8}$ alkynyl;
—$CONR^4R^5$ where $R^4$ and $R^5$ independently are H, $C_{1-8}$ alkyl, $C_{3-8}$ cycloalkyl, $C_{1-4}$ perhaloalkyl, or phenyl;
—$COR^4$;
$S(O)_nR^4$ where n=0–2;
—$OCOR^4$;
—$NR^4(CO)NHR^5$;
—$NR^4R^5$;
CN
$NO_2$;
halo;
perhalo $C_1-C_4$alkyl;
—$CO_2R^4$;
phenyl;
and pharmaceutically acceptable salts thereof.

2. A compound of claim 1 wherein said aryl radical is phenyl.

3. A compound of claim 1 wherein said substituents are selected from: hydrogen;
$C_{1-8}$ straight or branched alkyl;
—$CONR^4R^5$ where $R^4$ and $R^5$ independently are H, $C_{1-8}$ alkyl, $C_{1-4}$ perhaloalkyl;
—$COR^4$;
—$OCOR^4$;
—$NR^4(CO)R^5$;
—$NR^4(CO)NHR^5$;
—$NHSO_2R^4$;
—$OR^4$;
—$NR^4R^5$;
CN;
$NO_2$;
halo;
perhalo $C_1-C_4$alkyl;
—$CO_2R^4$.

4. A compound of claim 1 of the formula:

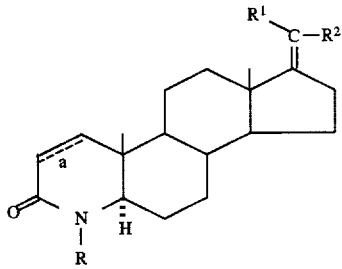

wherein the dashed line a represents a double bond when present,

R and $R^1$ are selected from hydrogen, methyl and ethyl; and $R^2$ is as defined in claim 1, including both (E) and (Z) forms, and mixtures thereof.

5. A compound of claim 4 where $R^1$ is methyl.

6. A compound of claim 4 where $R^1$ is hydrogen.

7. A compound of selected from:

4-methyl-24-nor-4-aza-5α-cholane-23-nitrile, (20R)-4-methyl-3-oxo-24-nor-4-aza-5α-cholane-23-nitrile, 4-methyl-3-oxo-4-aza-5α-pregnane-21-carbonitrile, 24-nor-4-aza-5α-chol-1-ene-23-nitrile, 24-nor-4-aza-cholane-23-nitrile, 4-methyl-24-nor-4-aza-5α-chol-1-ene-23-nitrile, 3-oxo-4-aza-5α-pregn-1-en-21-carbonitrile, 3-oxo -4-aza-5α-pregnane-21-carbonitrile, 4-methyl-3-oxo-4-aza-5α-pregnane-21-nitrile, 4-methyl-3-oxo-4-aza-5α-cholane-24-nitrile, 3-oxo-4-aza-5α-chol-1-ene-24-nitrile, 4-methyl-3-oxo-21-nor-4-aza-5α-cholane-24-nitrile, 3-oxo-21-nor-4-aza-5α-cholane-24-nitrile, 20,20-dimethyl-3-oxo-4-aza-5α-preg-1-ene-21-nitrile, and 3-oxo-4,20,20-trimethyl-4-aza-5α-pregnane-21-nitrile.

8. The compound according to claim 1 wherein:

Alk is selected from ethenyl, propenyl, isopropenyl, 1-butenyl, and 2-butenyl.

9. A pharmaceutical composition comprising 0.5 to 1000 mg of the compound of claim 1 in a pharmaceutically acceptable carrier therefor.

* * * * *